United States Patent [19]
Glaser et al.

[11] Patent Number: 5,256,770
[45] Date of Patent: Oct. 26, 1993

[54] OXIDATION RESISTANT THROMBOMODULIN ANALOGS

[75] Inventors: Charles B. Glaser; Michael J. Morser, both of San Francisco; David R. Light, San Mateo, all of Calif.

[73] Assignee: Schering AG, Berlin, Fed. Rep. of Germany

[21] Appl. No.: 506,325

[22] Filed: Apr. 9, 1990

[51] Int. Cl.$^5$ .............................................. C07K 13/00
[52] U.S. Cl. ................................. 530/381; 435/69.6; 530/380
[58] Field of Search ............... 530/381, 380; 435/69.6, 435/320.1; 536/27; 514/12

[56] References Cited

U.S. PATENT DOCUMENTS 4,752,585  6/1988  Koths et al. ......................... 435/256

FOREIGN PATENT DOCUMENTS

88/05053  7/1988  European Pat. Off. .
290419  11/1988  European Pat. Off. .
90/00955  2/1990  PCT Int'l Appl. .

OTHER PUBLICATIONS

Suzuki et al. "Structure and expression of human thrombomodulin . . . " EMBO 6(7):1891-1897, Jul. 1987.

Esmon, N. L., et al., "Isolation of a Membrane-bound Cofactor for Thrombincatalyzed Activation of Protein C," J. Biol. Chem. 257:859-864 (1982).

Salem, H. H., et al., "Isolation and Characterization of Thrombomodulin from Human Placenta," J. Biol. Chem. 259:12246-12251.

Jackman, R. W., et al., "Characterization of a thrombomodulin cDNA reveals structural similarity to the low density lipoprotein receptor," PNAS 83:8834-8839 (1986).

Jackman, R. W., et al., "Human thrombomodulin gene is intron depleted: Nucleic acid sequences of the cDNA and gene predict protein structure and suggest sites of regulatory control," PNAS 84:6425-6429 (1987).

Wen, D., et al., "Human Thrombomodulin: Complete cDNA Sequence and Chromosome Localization of the Gene," Biochemistry 26:4350-4357 (1987).

Kurosawa, S., et al., "A 10-kDa Cyanogen Bromide Fragment from the Epidermal Growth Factor Homology Domain of Rabbit Thrombomodulin Contains the Primary Thrombin Binding Site," J. Biol. Chem. 263:5993-5996 (1988).

Zushi, M., et al., "The Last Three Consecutive Epidermal Growth Factor-like Structures of Human Thromobomodulin Comprise the Minimum Functional Domain for Protein C-activating Cofactor Activity and Anticoagulant Activity," J. Biol. Chem. 264(18):10351-10353 (1989).

Otani, H., et al., "In Vitro Study on Contribution of Oxidative Metabolism of Isolated Rabbit Hear Mitochondria to Myocardial Reperfusion Injury," Circulation Research 55(2):168-175 (1984).

Saldeen, T., "Clotting, Microembolism, and Inhibition of Fibrinolysis in Adult Respiratory Distress," (Symposium on Critical Illness) Surgical Clinics of N. America 63(2):285-304 (1983).

Idell, S., et al., "Local Abnormalities in Coagulation and Firbinolytic Pathways Predispose to Alveolar Fibrin Deposition in the Adult Respiratory Distress Syndrome," J. Clin. Invest. 84:695-705 (1989).

Clark, R. A. F., et al., "Endothelial Cell Regulation of Coagulation," The Molecular and Cellular Biology of Wound Repair, 4:87-114 (1988).

Ishii, H., et al., "Thrombomodulin Is Present in Human Plasma and Urine," J. Clin. Inv. 76:2178-2181 (1985).

Stearns, D. J., et al., "Residues 310-486 from the Epidermal Growth Factor Precursor Homology Domain of Thrombomodulin will Accelerate Protein C Activation," J. Biol. Chem. 264:3352-3356 (1989).

Morser, M. J., "Soluble Thrombomodulin Analogs," U.S. Ser. No. 312,141, filed FEb. 17, 1989 (abandoned).

Morser, M. J., "Soluble Thrombomodulin Analogs," U.S. Ser. No. 345,372, filed Apr 28, 1989 (pending).

Morser, M. J., et al., "Analogs of Thrombomodulin," U.S. Ser. No. 406,941, filed Sep. 13, 1989 (pending).

Primary Examiner—Nina Ossanna
Attorney, Agent, or Firm—Townsend and Townsend Khourie and Crew

[57] ABSTRACT

Novel soluble oxidation resistant thrombomodulin analogs are produced for various therapeutic and other uses, such as in thrombotic and vascular disease therapies. These analogs exhibit the characteristic therapeutic properties of native thrombomodulin, yet they are soluble and are not inactivated after they have been exposed to oxidants. Some of the analogs disclosed are multifunctional fusion proteins having both antithrombotic activity and some additional bioactivity.

3 Claims, 5 Drawing Sheets

Figure 1A   Oxidation Resistant TM Analogs

Figure 1B   Multifuntional TM Analogs

FIG. 2.

COD #1033

```
    aa 456                aa 462
   ArgHis IleGlyThrAspCysSTOP
  (CGCCACATTGGCACCGACTGTTGA)  CODING SEQUENCE
   GCGGTGTAACCGTGGCTGACAACTCCTAGGGCC  PRIMER SEQUENCE
                — Bam HI SITE —
  CGCCACATTGGCACCGACTGTGACTCCGGCAAG  NATIVE SEQUENCE
```

COD #1034

```
       aa 227                 aa 234
      CysSerValGluAsnGlyGlyCys
  CCGGGATCCTGCAGCGTGGAGAACGGCGGCTGC  PRIMER/CODING SEQUENCE
     Bam HI
  GCTTGGGACTGCAGCGTGGAGAACGGCGGCTGC  NATIVE SEQUENCE
```

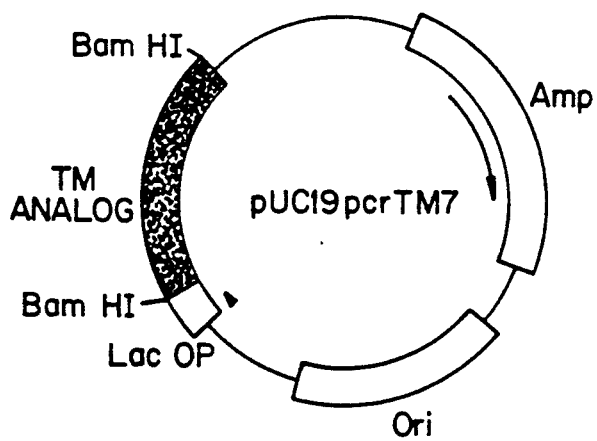

FIG. 4.
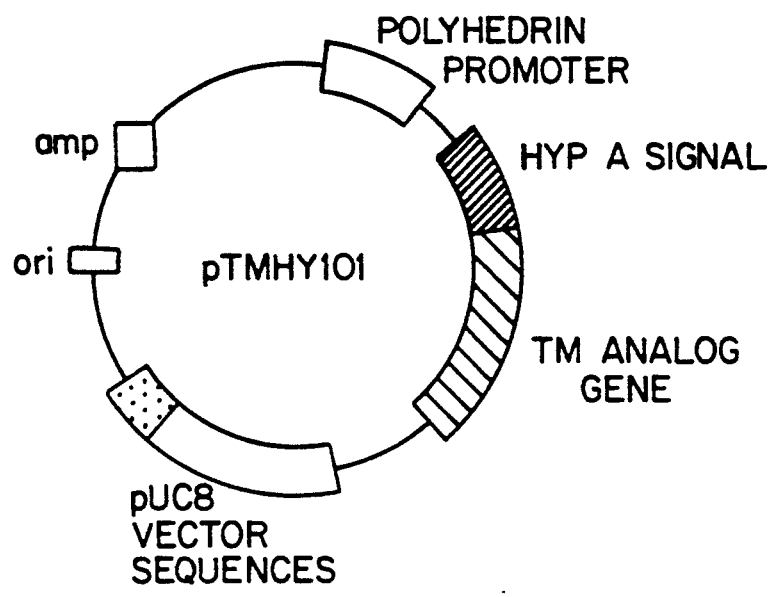
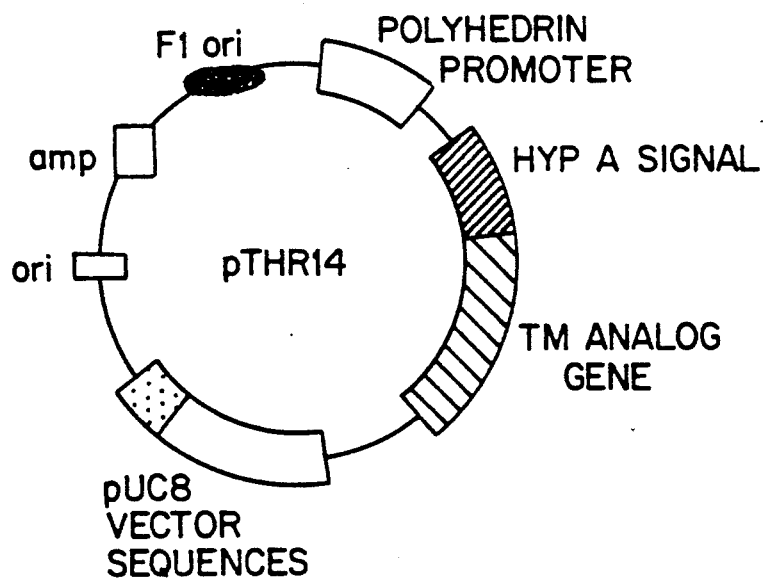

OXIDATION RESISTANT THROMBOMODULIN ANALOGS

BACKGROUND OF THE INVENTION

1. Field of the Invention

The present invention relates to the production and use of soluble analogs of thrombomodulin that retain activity after exposure to oxidants. These analogs are manufactured using recombinant DNA technology and are useful in, for example, antithrombotic therapy. Novel proteins, nucleic acid gene sequences, vectors, pharmaceuticals and methods of inhibiting thrombotic activity are disclosed.

2. Information Disclosure

There are many disease states that would benefit from treatment with a safe and effective anticoagulant/antithrombotic. The nature of these conditions varies. For example, anticoagulant therapy is useful in acute conditions such as during thrombolytic therapy in myocardial infarction or in treatment of disseminated intravascular coagulation (DIC) associated with, for example, septicemia. Anticoagulants are also useful for less acute conditions, such as chronic use in patients that have received heart valve implants or prophylactic use in surgery patients to reduce the risk of deep venous thrombosis (DVT). The anticoagulants currently approved for use in humans are not uniformly effective and a need exists for more efficacious compounds (See, for example, Prevention of Venous Thrombosis and Pulmonary Embolism, Consensus Development Conference Statement, NIH, 1986, 6(2):1-23).

Thrombomodulin is a membrane protein that has demonstrated anticoagulant properties. In humans, it is widely distributed on the endothelium of the vasculature and lymphatics except in the central nervous system. It functions as a receptor for thrombin, a central enzyme in the coagulation cascade. When free, thrombin promotes coagulation both directly by converting fibrinogen to fibrin and activating platelets, and indirectly through activation of other proteins in the coagulation cascade (Factors V, VIII and XIII, for example). When bound to thrombomodulin, however, the procoagulant activities of thrombin are inhibited, and its chief function is switched to the activation of protein C. Activated protein C in turn disrupts the coagulation process at several points. (See, for example, N Esmon, et al, (1982) $J.$ $Biol.$ $Chem.$ 257:859-864, H. Salem, et al, (1983) $J.$ $Biol.$ $Chem.$ 259:12246-12251).

The gene encoding native thrombomodulin has been isolated and sequenced from several species, both in its genomic form and as a cDNA (R. Jackman, et al, (1986) $PNAS$ 83:8834-8838 and (1987) 84:6425-6429, both of which are herein incorporated by reference). Comparisons with known proteins, such as the LDL receptor, have suggested functional domains (D. Wen, et al, (1987) $Biochemistry$ 26:4350-4357). One study has suggested that the fifth and sixth epidermal growth factor (EGF)-like domains have the capacity to bind thrombin (S. Kurosawa, et al, (1988) $J.$ $Biol.$ $Chem.$ 263:5993-5996; another suggests that EGF-like domains 4, 5, and 6 are sufficient to act as a cofactor for thrombin mediated protein C activating activity. (Zushi, et al, (1989) $J.$ $Biol.$ $Chem.$ 264:10351-10353).

Thrombomodulin in its natural form is not suitable for anticoagulant therapy as it is membrane-bound, due to its inherent amino acid sequence, and is insoluble without detergent treatment. It is present in such small amounts (about 300 mg thrombomodulin/person) that purification from autopsy or biopsy samples is impractical.

The inventors have also discovered that native thrombomodulin is susceptible to oxidation and when oxidized loses its ability to promote the activation of protein C. Many of the disease conditions requiring anticoagulation are also associated with high levels of toxic oxygen radicals, which can inactivate biomolecules and cause significant tissue damage. Examples of these conditions are reperfusion injury associated with myocardial infarction, DIC associated with septicemia, and alveolar fibrosis associated with adult respiratory distress syndrome. (See, Otani, H., et al, (1984) $Circ.$ $Res.$ 55:168-175, Saldeen, T., (1983) $Surg.$ $Clin.$ $N.A.$ 63(2):285-304, and Idell, S., et al, (1989) $J.$ $Clin.$ $Inv.$ 84:695-705.) In addition, any wound, such as occurring in surgical procedures, involves the influx of activated monocytes, polymorphonuclear leukocytes, etc. which can create toxic oxygen species as well as releasing a host of proteolytic enzymes, such as elastase. The connection between endothelial cell damage, inflammation and thrombosis has long been recognized (See $The$ $Molecular$ $and$ $Cellular$ $Biology$ $of$ $Wound$ $Repair.$ ed. Clark, R.A.F. and P.M. Henson 1988, for example). However, the inventors are the first to recognize that thrombomodulin is subject to inactivation by exposure to toxic oxygen species and that this likely plays a significant role in many pathogenic states.

Soluble thrombomodulin-like molecules have been detected at very low amounts in human plasma and urine. These molecules have a reduced ability to promote protein C activation, and it is possible that they have been rendered at least partially inactive, due at least in part to oxidation. It has been suggested that these molecules are degradation products of the membrane bound molecule (H. Ishii and P. Majerus, (1985) $J.$ $Clin.$ $Inv.$ 76:2178-2181), but they are present in such low amounts that they have been difficult to characterize ($\sim$0.8 mg/adult male). Proteolytic fragments of the purified native molecule have been produced using trypsin or elastase. (See, Ishii, supra, Kurosawa, et al, (1988) $J.$ $Biol.$ $Chem.$ 263:5593-5996 and Stearns, et al, (1989) $J.$ $Biol.$ $Chem.$ 264:3352-3356). Some of these fragments retain the ability to promote thrombin mediated activation of protein C in vitro.

Soluble analogs of thrombomodulin that retain most, if not all of, the activities of the native protein have been produced and are described in copending, coassigned applications U.S. Ser. No. 312,141 filed Feb. 17, 1989, U.S. Ser. No. 345,372 filed Apr. 28, 1989, U.S. Ser. No. 406,941 filed Sep. 13, 1989 and WO 90/00955 filed Feb. 16, 1990 and are herein incorporated by reference. Additional references include EP 290,419 and WO 88/05053, which discloses cDNA encoding the human thrombomodulin protein. Analogs of thrombomodulin have also been described in WO 88/05053, which discloses analogs with varying numbers of EGF-like domains.

There is a need for new compositions that exhibit the anticoagulant properties of thrombomodulin, are soluble in plasma, are resistant to inactivation by exposure to oxidants, and are easily produced in large quantities. The present invention fulfills these and other needs.

SUMMARY OF THE INVENTION

This invention provides peptides that have the characteristic antithrombotic activity of thrombomodulin but which are soluble in aqueous solution and are not inactivated after having been exposed to oxidants. These peptides, referred to as analogs, are lacking at least the membrane spanning and cytoplasmic domains of native thrombomodulin (see Table 1) and in addition have had specific amino acids of the native sequence removed or replaced by one or more different amino acids. Specifically, the amino acids removed or replaced are either one or both of the methionine residues at positions 291 or 388 in the native protein sequence. (See Table 1). In a preferred embodiment, either or both of these methionines are replaced with the amino acids alanine, leucine or glutamine. Replacing these methionines not only creates a peptide that retains activity after exposure to oxidants, but the novel peptide may exhibit an increased specific activity when compared to an equivalent peptide not having an amino acid substitution. Also provided are nucleotide sequences encoding the oxidation resistant TM analog peptides and recombinant vectors containing these novel nucleotide sequences. Methods for producing these peptides in both prokaryotic and eukaryotic cells are disclosed.

In particular, this invention provides for a thrombomodulin analog peptide that retains biological activity after exposure to oxidants at a concentration of oxidants and under conditions which eliminate biological activity of native thrombomodulin. It is preferred that the thrombomodulin analog peptide comprise a peptide having at least one amino acid of the native peptide sequence that has been replaced by one or more different amino acids. The preferred amino acid substitutions are of the methionine residues described above. Most preferred is the substitution of the methionine at position 388 with either a peptide bond (deletion) or with one or more amino acids which are unaffected by oxidants. The preferred substitutes for the methionine residues are amino acids selected from the group consisting of leucine, glutamine and alanine. It is also preferred that the analogs described above have the same or an higher specific activity as the native thrombomodulin. Specific activity is typically measured by the peptides ability to bind thrombin and enhance the thrombin mediated activation of protein C.

This invention also provides for multifunctional TM analogs comprised of a thrombomodulin analog peptide as described above and a second functional component. It is preferred that the second functional component have fibrinolytic activity such as a t-PA-like protein. The second functional component may be a means of binding a peptide to a biocompatible polymer.

This invention further provides for sequences of nucleic acids encoding a thrombomodulin analog peptide that retains activity after exposure to oxidants. The peptides are as described above and may include sequences encoding the proteinaceous second functional components such as tissue plasminogen activator-like proteins. The sequences may be combined into a recombinant vector such as extra chromosomal plasmid or transfection vector capable of incorporation into the genome of the cell hosting the recombinant vector. The sequences may be operably linked to a promoter to permit the host cell to express the desired analog peptide. Both eukaryotes and prokaryotes are disclosed as suitable host cells for these recombinant vectors.

This invention further provides for pharmaceutical compositions having antithrombotic activity comprising a sterile preparation of a unit dose of the thrombomodulin analog peptides as described above. There is also provided herein, methods for using the pharmaceutical compositions for controlling thrombotic activity in a mammal by administering an effective amount of the compositions. The pharmaceutical compositions also include the multifunctional components described above. In addition, these compositions also include a biocompatible polymer having a surface wherein the surface has bound thereto a thrombomodulin analog peptide that retains biological activity after exposure to oxidants at a concentration and under conditions which eliminate biological activity of the native thrombomodulin.

A further method for preventing thrombosis in a human is described herein. The method comprises intravenously administering a dose of 0.001 to 0.1 mg of an oxidation resistant thrombomodulin analog peptide per kilogram of body weight in a pharmaceutically acceptable salt solution. The analogs are as described above.

BRIEF DESCRIPTION OF THE FIGURES

FIG. 4 depicts baculovirus transfer vector pTMHY101 and a vector for making single-stranded DNA for use in site directed mutagenesis reactions, pTHR14.

DETAILED DESCRIPTION

Figure 1:
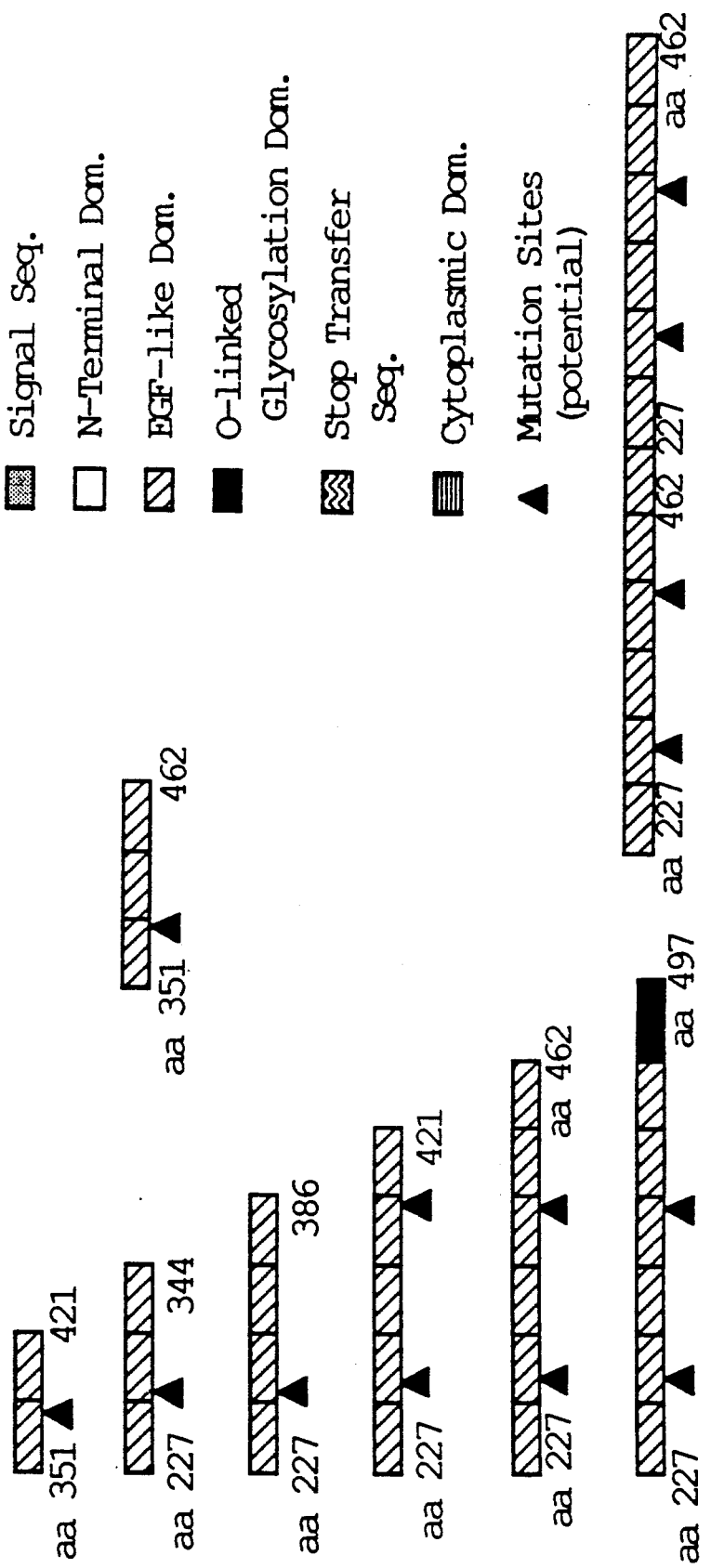
FIGS. 1A and 1B schematically illustrate the domains of native thrombomodulin, the regions of the native molecule comprised in the soluble oxidation resistant TM analogs of this invention, the possible mutation sites in each analog peptide, and multifunctional mutant analog peptides.

The present invention provides novel compositions which exhibit substantially all of the properties of native thrombomodulin but which are soluble in plasma and retain activity after exposure to oxidants. Also provided are methods of producing these compositions. The following detailed description sets forth these and other aspects of this invention.

Thrombomodulin, or TM, is an endothelial cell membrane protein that acts as a receptor for thrombin. It can be released from the cell membrane in the presence of sufficient detergent and retains the ability to bind to thrombin in solution. When bound to thrombomodulin, thrombin is converted from a procoagulant enzyme to an anticoagulant enzyme. In particular, the thrombin mediated activation of protein C is greatly enhanced when thrombin is bound to thrombomodulin i.e., the rate of protein C activation increases at least 1000 fold when thrombin is bound to thrombomodulin.

The inventors have discovered that the activity of thrombomodulin is compromised after it has been exposed to oxidants. Examples of physiological oxidants are superoxide and hydroxyl radicals and related species such as hydrogen peroxide and hypohalous acid. Oxygen free radical intermediates, such as superoxide and hydroxyl radicals, are produced through normal and pathologic metabolic processes. Other important toxic oxidants are chloramines, formed by the reaction of hypochlorite with ammonia or amines. See Dvorak, H.F., et al, in *The Molecular Biology of Wound Repair*, Clark, R.A.F. and P.M. Henson eds., (1988) p 165-172. Biological macromolecules such as thrombomodulin can serve as targets for the damaging actions of these oxidants.

Oxidation damage to tissues is known to be involved in the pathophysiology of a number of human diseases including acute respiratory distress syndrome, reperfusion injury, immune injury to the lung and kidneys, cerebral trauma or ischemia, atherosclerosis, and rheumatoid arthritis. Oxidative inactivation of a variety of soluble proteins, as well as membrane lipids, has been linked to the regulation of both normal processes and to disease states. For example, oxidative inactivation of alpha-1-protease inhibitor in the lungs of smokers' is an important contributor to the lung proteolysis characteristic of pulmonary emphysema (Carp, H., et al, (1982) *PNAS* 79:2041-2045). Reperfused myocardial tissues following thrombolytic therapy suffer significant injury from superoxide radicals generated by enzymatic reactions in the affected tissues. Inflammation of the postischeamic tissue results in the infiltration of phagocytes, including neutrophils and monocytes, which themselves produce large amount of superoxide radicals, as well as hydroxyl radicals, hydrogen peroxide, hypohalides, and long-lasting N-chloramines. (McCord, J.M., (1987) *Fed. Proc.* 46:2402-2406, Henson, P.M. and R.B. Johnston,(1987) *J. Clin. Inv.* 79:669-674, Weiss, S.J., et al, (1983) *Science* 222:623-628).

The inventors have discovered that thrombomodulin is susceptible to reaction with oxidants and that such a reaction destroys thrombomodulin's antithrombotic activity. For example, cultured human cells (A549) rapidly lose the ability to enhance the activation of protein C through thrombin after they have been exposed to activated monocytes or chemical oxidants such as chloramine-T. A549 cells (CCL 185, Giard, et al, (1972) *J. Natl. Cancer Inst.* 51:1417-1423) have about 10,000 molecules of membrane bound thrombomodulin per cell. The inventors have also demonstrated that solubilized purified native thrombomodulin loses its activity when incubated with chloramine-T. Experiments with fragments of native thrombomodulin containing the 6 EGF-like domains have shown that binding to thrombin does not protect thrombomodulin from oxidation. Two specific amino acids, the methionines at positions 291 and 388 (see Table 1), are oxidized and when these amino acids are oxidized the TM fragment loses activity. The peptides of the present invention have other amino acids substituted for the methionines at positions 291 and/or 388.

Many of the pathologic states associated with activated oxygen radical generation are conditions in which an antithrombotic such as a soluble TM analog would be a useful therapeutic. It is highly desirable, therefore, to have a safe effective antithrombotic that retains activity, such as protein C activation cofactor activity for example, after exposure to oxidants. In the present invention this is accomplished by substituting one or more amino acids in the native thrombomodulin sequences that are susceptible to oxidation (or removing them entirely) with amino acids that are resistant to oxidation without altering the biological activity of the peptide. One of skill could understand that there is a limit to the total number of amino acids that can be used to replace a single amino acid in a protein, this limit being defined by the retention of activity. These peptides would have increased utility and stability in vivo as well as increased shelf-life. The specific activity may be increased as compared to the wild type (non-mutant) TM analog peptide.

A sequence of DNA encoding human thrombomodulin has been isolated. It encodes a protein of 575 amino acids (~60.3 kDa), which includes an 18 amino acid signal sequence. Thrombomodulin gene sequences isolated from different species (bovine, mouse, human) exhibit a high degree of sequence homology. The entire DNA and amino acid sequence of human thrombomodulin is shown in Table 1. The definition of thrombomodulin used herein includes the natural allelic variations that may exist between individuals.

By comparison and analogy with the sequences of other known proteins, thrombomodulin can be divided into six functional domains. A domain is a three dimensional, self-assembling array of amino acids of a protein molecule, which contains structural elements necessary for a specific biological activity of that protein.

| Approximate Amino Acid Position | Domain |
|---|---|
| −18-1 | signal peptide |
| 1-226 | N-terminal domain - homologous to some lectins |
| 227-462 | repeats of EGF-like domains |
| 463-497 | O-linked glycosylation domain |
| 498-521 | stop transfer domain - membrane spanning |
| 522-557 | cytoplasmic domain |

See C.S. Yost, et al, (1983) *Cell* 34:759-766 and D. Wen, et al, (1987) *Biochemistry* 26:4350-4357, both herein incorporated by reference.

Oxidants, in general, are highly reactive chemical species. In their quest for electrons, oxidants will react with a variety of molecules, both biological and nonbiological. Of the amino acids that make up proteins, histidine, methionine, cysteine, tryptophan, and arginine are the most likely to be oxidized. In the case of thrombomodulin, the reaction of the methionines at positions 291 and 388 to form methionine sulphoxide is a particular problem resulting in the loss of thrombomodulin's antithrombotic activity. Not only does the loss of this activity allow coagulation processes to go unchecked, oxidized proteins may be more rapidly digested by proteases (Starke-Reed, P.E. and C.N. Oliver, (1989) *Arch. Biochem. Biophys.* 275:559-567 and Davies, K.J.A., et at, (1987) *J. Biol. Chem.* 262(20):9914-9920) possibly allowing membrane bound thrombomodulin to be cleaved off by, for example, the elastase secreted by activated neutrophils.

The proteins of this invention are analogs of thrombomodulin (TM). By this it is meant that they are proteins having substantially the same characteristic biological activity of native thrombomodulin as defined below, further characterized by the fact that they are soluble in an aqueous solution and by the presence of a specific artificially induced mutation in their amino acid sequence.

Methods for rendering amino acids, specifically methionines, resistant to oxidation are well known in the art. It is possible to chemically modify thiol groups with iodoacetic acid, for example, to form oxidation resistant sulphonium (Gundlach, H.G., et al, (1959) *J. Biol. Chem.* 234:1754). A preferred method is by removing the susceptible amino acid or replacing it with one or more different amino acids that will not react with oxidants. The amino acids leucine, alanine and glutamine would be particularly preferred amino acids because of their size and neutral character.

Methods by which amino acids can be removed or replaced in the sequence of a protein are well known. Genes that encode a peptide with an altered amino acid sequence can be made synthetically, for example. A preferred method is the use of site directed in vitro mutagenesis. Site-directed mutagenesis involves the use of a synthetic oligodeoxyribonucleotide containing a desired nucleotide substitution, insertion or deletion designed to specifically alter the nucleotide sequence of a single-strand target DNA. Hybridization of this oligonucleotide, also called a primer, to the single-strand template and subsequent primer extension produces a heteroduplex DNA which when replicated in a transformed cell, will encode a protein sequence with the desired mutation. This method is outlined in detail in the Examples below and depicted in FIG. 3.

It is critical, of course, that the removal or substitution allow the mutant peptide to retain biological activity. Thrombomodulin activity can be determined in a variety of assays that depend on alterations in the action of thrombin. A particularly preferred activity is the ability of thrombomodulin, or its soluble analogs, to accelerate the thrombin catalyzed activation of protein C, as this ability is unique to thrombomodulin. Protein C cofactor activity can be measured in the assay described by Salem, et al, (1984) *J. Biol. Chem.* 259(19):12246–12251 and Galvin, et al, (1987) *J. Biol. Chem.* 262(5):2199–2205. In brief, this assay consists of two steps. The first is the incubation of the test oxidation resistant TM analog with thrombin and protein C under defined conditions (see Examples below). In the second step, the thrombin is inactivated with hirudin or antithrombin III and heparin, and the activity of the newly activated protein C is determined by the use of a chromogenic substrate, whereby the chromophore is released by the proteolytic activity of activated protein C. This assay is carried out with purified reagents.

Alternatively the effect of an oxidation resistant TM analog can be measured using plasma in clotting time assays such as the activated partial thromboplastin time (APTT), thrombin clotting time (TCT) and/or prothrombin time (PT). These assays distinguish between different mechanisms of coagulation inhibition, and involve the activation of protein C. Prolongation of the clotting time in any one of these assays demonstrates that the molecule can inhibit coagulation in plasma.

To determine the resistance to loss of thrombomodulin activity due to oxidation, the test material (100–250 μg/ml) is first incubated with an oxidant such as, for example, chloramine-T, hydrogen peroxide at 5–10 mM chloramine-T or 200–1000 mM hydrogen peroxide in a buffer of 0.2% N-ethylmorpholine and 0.008% Tween 80 at pH 7.0 for 20 minutes at room temperature. After such oxidant exposure, the test material is evaluated using one of the assays described above. Those mutant TM analogs that retain at least 60%, and preferably 90%, of activity they had prior to exposure to oxidants are considered to be oxidation resistant as compared to wild-type (non-mutant) TM analog or native thrombomodulin. Some of the mutant TM analogs may demonstrate an increase in specific activity compared to the wild-type peptide even without exposure to oxidants. This may be the result of a low level of inherent oxidation in the wild-type peptide or an actual alteration in the interaction between thrombin and the mutant analog due to the change in amino acids. Details of these assays are provided in the Examples below.

The above assays are used to identify soluble oxidation resistant TM analogs that are able to bind thrombin and to activate protein C in both purified systems and in a plasma milieu. Further assays are then used to evaluate the resistance to loss of other thrombomodulin activities such as inhibition of thrombin catalyzed formation of fibrin from fibrinogen (Jakubowski, et al, (1986) *J. Biol. Chem.* 261(8):3876–3882), inhibition of thrombin activation of Factor V (Esmon, et al, (1982) *J. Biol. Chem.* 257:7944–7947), accelerated inhibition of thrombin by antithrombin III and heparin cofactor II (Esmon, et al, (1983) *J. Biol. Chem.* 258:12238–12242), inhibition of thrombin activation of Factor XIII (Polgar, et al, (1987) *Thromb. Haemostas.* 58:140), inhibition of thrombin mediated inactivation of protein S (Thompson and Salem, (1986) *J. Clin. Inv.* 78(1):13–17) and inhibition of thrombin mediated platelet activation and aggregation (Esmon, et al, (1983) *J. Biol. Chem.* 258:12238–12242).

Use of Oxidation Resistant TM Analogs as an Anticoagulant/ Antithrombotic

The underlying pathology of thrombotic disorders is that a clot forms in response to a stimulus such as, for example, a damaged vessel wall. This stimulus triggers the coagulation cascade generating thrombin, which has the ability to convert fibrinogen to fibrin, the matrix of the clot.

Soluble oxidation resistant TM analogs administered systemically will protect against thrombus formation because they will inhibit the generation of thrombin, via the activated Protein C system, and/or inhibit the action of thrombin on fibrinogen without disturbing other coagulation parameters. Thus, the use of soluble oxidation resistant TM analogs will be both safe and effective at preventing unwanted thrombus formation. The effect of thrombomodulin can be overcome by the large amounts of thrombin generated by a serious injury to vessels allowing a hemostatic plug to form.

Diseases in which thrombus formation plays a significant etiological role include myocardial infarction, disseminated intravascular coagulation, deep vein thrombosis, pulmonary embolism, septic shock, acute respiratory distress syndrome, unstable angina and other arterial and venous occlusive conditions. In all of these, as well as in other diseases in which thrombus formation is pathological, soluble oxidation resistant TM analogs alone or in combination with thrombolytics are useful for treatment, either to cure the disease or to prevent its progression to a more severe state. Soluble oxidation resistant TM analogs also provide a safe and effective anticoagulant, for example, in patients receiving bioprostheses such as heart valves or patients requiring extracorporeal circulation. These compounds may replace heparin and warfarin in the treatment of, for example, pulmonary embolism or acute myocardial infarction.

Angioplasty is a procedure frequently used for restoring patency in occluded arteries. Although patency may be restored, this procedure often damages the endothelial lining of the artery, and blood clots begin to form as a result. Damage to the endothelium starts a process whereby activated leukocytes are recruited to the site. These activated leukocytes release, among other things, oxidants such as peroxides, which can destroy the activity of native membrane bound thrombomodulin in the effected area, thus contributing to the local procoagulant state. Soluble oxidation resistant TM analogs administered in conjunction with angioplasty will prevent this deleterious side effect.

Many acute thrombotic and embolic diseases are currently treated with fibrinolytic therapy in order to remove the thrombus. The condition that has been most widely investigated is acute myocardial infarction (heart attack). Agents currently in use for treating acute myocardial infarction include streptokinase, tissue plasminogen activator and urokinase. Use of these agents can lead to serious bleeding complications. Patients who have had a thrombus removed by fibrinolytic therapy and in whom the blood flow has been restored frequently reocclude the affected vessel, i.e., a clot reforms. Attempts have been made to prevent reocclusion by increasing the dose or duration of treatment with a thrombolytic agent, but the incidence of bleeding then increases.

Complicating myocardial infarction is the tissue damage associated with reperfusion. As the thrombus is dissolved, oxygen radicals are generated at the clot site, destroying surrounding tissue and initiating a neutrophil-dependent inflammatory response. (Simpson, P.J., et al, in *An Upjohn Symposium on Oxygen Radicals,* April 1987, pg. 63-69). The use of soluble oxidation resistant TM analogs that are not inactivated by these oxygen radicals provides protection against reocclusion by virtue of its antithrombotic activity. Its specific action is local rather than systemic, i.e., where thrombin is being generated or being released from a clot. Therefore, when used in combination with a thrombolytic agent, whose dose can then be decreased, the risk of bleeding can be substantially reduced.

It is important to note that many, if not most, of the conditions which require the use of an anticoagulant, antithrombotic and/or fibrinolytic pharmaceutical are also conditions associated with the production of active oxygen radicals. It is impossible to predict with certainty if a particular protein will be susceptible to oxidation, and if oxidized one of skill would not expect oxidation to result in inactivation of the protein. Thrombomodulin is completely inactivated. Loss of activity would necessitate an increase in dose, with a concomitant increase in possible side effects. A protein pharmaceutical immune to loss of activity from oxidation would, therefore, be highly desirable for use in these conditions.

Administration of soluble oxidation resistant TM analogs would be by a bolus intravenous injection, by a constant intravenous infusion or by a combination of both routes. Also, oxidation resistant TM analogs mixed with appropriate excipients may be taken into the circulation from an intramuscular site. As used herein, a therapeutically effective dose is defined as that level of oxidation resistant TM analog required to prevent formation of pathological clots.

Systemic treatment with oxidation resistant TM analogs can be monitored by determining hemostatic parameters such as the activated partial thromboplastin time (APTT) on serial samples of blood taken from the patient. The coagulation time observed in this assay is prolonged when a sufficient level of oxidation resistant TM analog is achieved in the circulation. However, this is a systemic measurement of efficacy, and perhaps a dose that is effective at the site of a clot would not be effective in prolonging the APTT. Dosing levels and regimens can be adjusted so that an adequate concentration of active protein is maintained as measured by, for example, the APTT assay or the protein C activation assay.

In one aspect of the invention, the oxidation resistant TM analogs described are secreted from the eukaryotic cells in which they are produced. For pharmacological administration, the oxidation resistant TM analog may optionally be combined with phospholipid vesicles, detergents or other similar compounds well known to those skilled in the art of pharmacological formulation. The oxidation resistant TM analogs of the present invention are soluble in the blood stream, making the analogs useful in various anticoagulant and other therapies.

In contrast to full length thrombomodulin, the analogs of this invention should offer an improved pharmaceutical both by virtue of their solubility, stability, and superior activity. It is anticipated that these analogs will offer superior characteristics from a manufacturing perspective, a pharmaceutical perspective or both.

General Methods

Generally, the definitions of nomenclature and descriptions of general laboratory procedures used in this application can be found in T. Maniatis et al. *Molecular Cloning, A Laboratory Manual,* (1982) Cold Spring Harbor Laboratory, Cold Spring Harbor, New York. The manual is hereinafter referred to as Maniatis and is hereby incorporated by reference.

All enzymes were used according to the manufacturer's instructions.

Oligonucleotides that are not commercially available can be chemically synthesized according to the solid phase phosphoramidite triester method first described by S.L. Beaucage and M.H. Caruthers, (1981) *Tetrahedron Letts.,* 22(20):1859-1862 using an automated synthesizer, as described in D.R. Needham-VanDevanter et al. (1984) *Nucleic Acids Res.,* 12:6159-6168. Purification of oligonucleotides was by either native acrylamide gel electrophoresis or by anion-exchange HPLC as described in J.D. Pearson and F.E. Regnier, (1983) *J. Chrom.,* 255:137-149. Nucleotide sizes are given in either kilobases (kb) or base pairs (bp). These are estimates derived from agarose or acrylamide gel electrophoresis or from published DNA sequences.

The sequence of the cloned genes and synthetic oligonucleotides can be verified using the chemical degradation method of A.M. Maxam et al. (1980) *Methods in Enzymology,* 65:499-560. The sequence can be confirmed after the assembly of the oligonucleotide fragments into the double-stranded DNA sequence using the method of Maxam and Gilbert, supra, or the chain termination method for sequencing double-stranded templates of R.B. Wallace et al. (1981) *Gene,* 16:21-26. Southern Blot hybridization techniques were carried out according to Southern et al. (1975) *J. Mol. Biol.,* 98:503.

This invention relates to the creation of novel peptides and genes by in vitro mutagenesis. Target genes are isolated in intermediate vectors and cloned for amplification in prokaryotes such as *E. coli.* Bacillus or Streptomyces. Most preferred is *E. coli* because that organism is easy to culture and more fully understood than other species of prokaryotes. The Maniatis manual contains methodology sufficient to conduct all subsequently described clonings in *E. coli.* Strain MH-1 is preferred unless otherwise stated. All *E. coli* strains are grown on Luria broth (LB) with glucose, or M9 medium supplemented with glucose and acid-hydrolyzed casein amino acids. Strains with resistance to antibiotics were maintained at the drug concentrations described in Maniatis. Transformations were performed according to the method described by D.A. Morrison, (1977) *J. Bact.*, 132:349–351 or by J.E. Clark-Curtiss and R. Curtiss, (1983) *Methods in Enzymology*, 101:347–362, Eds. R. Wu et al., Academic Press, New York. Representative vectors include pBR322 and the pUC series which are available from commercial sources.

Definitions

For purposes of the present invention the following terms are defined below.

The term "vector" refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). The term "transfer vector" refers to a vector cotransfected into an insect cell with a wild-type baculovirus. The transfer vector is constructed in such a way as to encourage a recombination between the baculovirus genome and the transfer vector, replacing the baculovirus polyhedrin gene with a heterologous target gene. Where a vector is being maintained by a host cell, the vector may either be stably replicated by the cells during mitosis as an autonomous structure, or is incorporated within the host's genome.

The term "promoter" is a region of DNA involved in binding the RNA polymerase to initiate transcription.

The term "operably linked" refers to a juxtaposition wherein the components are configured so as to perform their usual function. Thus, control sequences or promoters operably linked to a coding sequence are capable of effecting the expression of the coding sequence.

The term "control sequence" refers to a DNA sequence or sequences which are capable, when properly ligated to a desired coding sequence, of affecting its expression in hosts compatible with such sequences. Such control sequences include at least promoters in both prokaryotic and eukaryotic hosts, and optionally, transcription termination signals. Additional factors necessary or helpful in effecting expression may also be identified. As used herein, "control sequences" simply refers to whatever DNA sequence may be useful to result in expression in the particular host used.

The term "oxidant" refers to a chemical reagent that removes electrons from a molecule (or atom). Examples of physiological oxidants are hydroxyl radical and hydrogen peroxide, among many others.

The term "native" thrombomodulin refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "specific artificially induced mutation" includes deletions, insertions and substitutions in the amino acid sequence, which may be introduced through manipulation of a cloned DNA sequence. The DNA sequence encoding a mutant TM analog is referred to as a "mutant DNA sequence".

Gene Synthesis

Publication of the full length DNA sequence encoding human thrombomodulin facilitates the preparation of genes and is used as a starting point to construct DNA sequences encoding soluble mutuant TM analogs. The analogs of the present invention are soluble derivatives which lack a stop transfer sequence in addition to having internal amino acid substitutions. Furthermore, these analogs are secreted from eukaryotic cells which have been transfected or transformed with plasmids containing genes which encode these polypeptides. Methods for making modifications, such as amino acid substitutions, deletions, or the addition of signal sequences to cloned genes are known. Specific methods used herein are described below.

The full length gene for thrombomodulin can be prepared by several methods. Human genomic libraries are commercially available. Oligonucleotide probes, specific to the thrombomodulin gene, can be synthesized using the published gene sequence. Methods for screening genomic libraries with oligonucleotide probes are known. The publication of the gene sequence for thrombomodulin demonstrates that there are no introns within the coding region. Thus a genomic clone provides the necessary starting material to construct an expression plasmid for thrombomodulin using known methods.

A thrombomodulin encoding DNA fragment can be retrieved by taking advantage of restriction endonuclease sites which have been identified in regions which flank or are internal to the gene. (R.W. Jackman et al. (1987) *Proc. Natl. Acad. Sci. USA.*, 84:6425–6429).

Alternatively, the full length gene is obtained from a cDNA bank. Messenger RNA prepared from endothelial cells provides suitable starting material for the preparation of cDNA. A cDNA molecule containing the gene encoding thrombomodulin is identified as described above. Methods for making cDNA banks are well known (See Maniatis).

Genes encoding soluble oxidation resistant TM analogs may be made from wild-type TM analog genes first constructed using the gene encoding full length thrombomodulin. A preferred method for producing wild-type TM analog genes for subsequent mutation combines the use of synthetic oligonucleotide primers with polymerase extension on a mRNA or DNA template. This desired nucleotide sequence. U.S. Pat. Nos. 4,683,195 and 4,683,202 describe this method. Restriction endonuclease sites can be incorporated into the primers. Genes amplified by the PCR reaction can be purified from agarose gels and cloned into an appropriate vector. Alterations in the natural gene sequence can be introduced by the techniques of in vitro mutagenesis or by use of the polymerase chain reaction with primers that have been designed to incorporate appropriate mutations.

The soluble oxidation resistant TM analogs described herein are secreted when expressed in eukaryotic cell culture. Secretion may be obtained by the use of the native signal sequence of the thrombomodulin gene. Alternatively, genes encoding the soluble oxidation resistant TM analogs of the present invention may be ligated in proper reading frame to a signal sequence other than that corresponding to the native thrombomodulin gene. For example, the signal sequence of t-PA, (see commonly assigned co-pending U.S. Ser. No. 074,083 filed Jul. 16, 1987 incorporated herein by reference) or of hypodermin A or B (see commonly assigned co-pending U.S. Ser. No. 148,749, filed Jan. 27, 1989 incorporated hereby by reference) can be linked to the polypeptide (See Table 2). In the preferred embodiment of the present invention, use is made of the signal sequence of t-PA which contains the second intron of the human t-PA gene. The inclusion of the intron enhances the productivity of the adjacent structural gene (see commonly assigned co-pending U.S. Ser. No. #003,611 filed Jan. 14, 1987 incorporated herein by reference).

With the analogs of this invention, those portions of the gene encoding the stop transfer and cytoplasmic domains of the carboxyl terminal region of the native thrombomodulin gene are deleted. Therefore, it is necessary to add a stop codon so that translation will be terminated at the desired position. Alternatively, a stop codon can be provided by the desired expression plasmid. Additionally a polyadenylation sequence is necessary to ensure proper processing of the mRNA in eukaryotic cells encoding the oxidation resistant TM analog. Also, it may be necessary to provide an initiation codon, if one is not present, for expression of the soluble oxidation resistant TM analog. Such sequences may be provided from the native gene or by the expression plasmid.

The thrombomodulin analogs of this invention are described by their amino acid sequences and by their DNA sequence, it being understood that the analogs include their biological equivalents such that this invention includes minor or inadvertent substitutions and deletions of amino acids that have substantially little impact on the biological properties of the analogs. It should also be understood that alternative sequences could be used to express soluble oxidation resistant TM analogs in various host cells. Furthermore, due to the degeneracy of the genetic code, equivalent codons may be substituted to encode the same polypeptide sequence.

Cloning Vectors

Cloning vectors suitable for replication and integration in prokaryotes or eukaryotes and containing transcription and translation terminators, initiation sequences, and promoters useful for regulation of the expression of soluble oxidation resistant TM analogs are described herein. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems.

Expression of Soluble Oxidation Resistant TM Analogs in Prokaryotic Cells

In addition to the use of cloning methods in *E. coli* for amplification of cloned sequences it may be desirable to express oxidation resistant TM analogs in prokaryotes. The inventors have discovered that the carbohydrate moieties of the mature protein are not essential for activity as a cofactor and do have an effect on the molecule's half life in circulation. Expression of thrombomodulin analogs in *E. coli* has provided a useful tool for analysis of this issue. It protein from *E. coli* transformed with an expression plasmids encoding a soluble oxidation resistant TM analog.

Methods for the expression of cloned genes in bacteria are well known. To obtain high level expression of a cloned gene in a prokaryotic system, it is essential to construct expression vectors which contain, at the minimum, a strong promoter to direct mRNA transcription termination. Examples of regulatory regions suitable for this purpose are the promoter and operator region of the *E. coli* β-galactosidase gene, the *E. coli* tryptophan biosynthetic pathway, or the leftward promoter from the phage lambda. The inclusion of selection markers in DNA vectors transformed in *E. coli* are useful. Examples of such markers include the genes specifying resistance to ampicillin, tetracycline, or chloramphenicol.

See Maniatis for details concerning selection markers and promoters for use in *E. coli*. In the described embodiment of this invention pUC19 is used as a vector for the subcloning and amplification of desired gene sequences.

Expression of Oxidation Resistant TM Analogs in Eukaryotic Cells

It is expected that those of skill in the art are knowledgeable in the expression systems chosen for expression of the desired oxidation resistant TM analog and no attempt to describe in detail the various methods known for the expression of proteins in eukaryotes will be made.

The DNA sequence encoding a soluble oxidation resistant TM analog can be ligated to various expression vectors for use in transforming host cell cultures. The vectors typically contain marker genes and gene sequences to initiate transcription and translation of the heterologous gene.

The vectors preferably contain a marker gene to provide a phenotypic trait for selection of transformed host cells such as dihydrofolate reductase, metallothionein, hygromycin, or neomycin phosphotransferase. The nuclear polyhedral viral protein from *Autographa californica* is useful to screen transfected insect cell lines from *Spodoptera frugiperda* and *Bombyx mori* to identify recombinants. For yeast, Leu-2, Ura-3, Trp-1, and His-3 are known selectable markers (*Gene* (1979) 8:17–24). There are numerous other markers, both known and unknown, which embody the above scientific principles, all of which would be useful as markers to detect those eukaryotic cells transfected with the vectors embraced by this invention.

Of the higher eukaryotic cell systems useful for the expression of soluble oxidation resistant TM analogs, there are numerous cell systems to select from. Illustrative examples of mammalian cell lines include RPMI 7932, VERO and HeLa cells, Chinese hamster ovary (CHO) cell lines, WI38, BHK, COS-7, C127 or MDCK cell lines. A preferred mammalian cell line is CHL-1. When CHL-1 is used hygromycin is included as a eukaryotic selection marker. CHL-1 cells are derived from RPMI 7932 melanoma cells, a readily available human cell line. The CHL-1 cell line has been deposited with the ATCC according to the conditions of the Budapest Treaty and has been assigned #CRL 9446, deposited Jun. 18, 1987. Cells suitable for use in this invention are commercially available from the American Type Culture Collection. Illustrative insect cell lines include *Spodoptera frugiperda* (fall Armyworm) and *Bombyx mori* (silkworm).

As indicated above, the expression vector, ex. plasmid, which is used to transform the host cell, preferably contains gene sequences to initiate the transcription and sequences to control the translation of the soluble oxidation resistant TM analog protein gene sequence. These sequences are referred to as expression control sequences. When the host cell is of insect or mammalian origin, illustrative expression control sequences include but are not limited to the following: the retroviral long terminal repeat promoters ((1982) *Nature*, 297:479–483), SV40 promoter ((1983) *Science*, 222:524–527, thymidine kinase promoter (J. Banerji et al. (1982) *Cell*, 27:299–308), or the beta-globin promoter (P.A. Luciw et al. (1983) *Cell*, 33:705–716). The recipient vector nucleic acid containing the expression control sequences is cleaved using restriction enzymes and adjusted in size as necessary or desirable. This segment is ligated to a DNA sequence encoding a soluble oxidation resistant TM analog by means well known in the art.

When higher animal host cells are employed, polyadenylation or transcription termination sequences need to be incorporated into the vector. An example of a polyadenylation sequence is the polyadenylation sequence from SV40, which may also function as a transcription terminator.

Genes incorporated into the appropriate vectors can be used to direct synthesis of proteins in either transient expression systems or in stable clones. In the former case yields are low, but the experiments are quick. In the latter case it takes more time to isolate high producing clones. Different vectors may be used for the two different types of experiments. In particular, in the case of transient expression, sequences may be included within the plasmid that allow the plasmid to replicate to a high copy number within the cell. These sequences may be derived from virus such as SV40 (e.g. C. Doyle et al. (1985) *J. Cell Biol.*, 100:704–714) or from chromosomal replicating sequences such as murine autonomous replicating sequences (Weidle et al. (1988) *Gene*, 73:427–437). The vector for use in transient expression should also contain a strong promoter such as the SV40 early promoter (e.g., A. van Zonnenfeld et al. (1987) *Proc. Natl. Acad. Sci. USA.*, 83:4670–4674) to control transcription of the gene of interest. While transient expression provides a rapid method for assay of gene products, the plasmid DNA is not incorporated into the host cell chromosome. Thus, use of transient expression vectors does not provide stable transfected cell lines. A description of a plasmid suitable for transient expression is provided by A. Aruffo & B. Seed, (1987) *Proc. Natl. Acad. Sci. USA.*, 84:8573–8577.

Soluble oxidation resistant TM analogs may alternatively be produced in the insect cell lines described above using the baculovirus system. This system has been described by V.A. Luckow and M.D. Summers (1988) *Bio/Technology*, 6:47–55. Generally, this expression system provides for a level of expression higher than that provided by most mammalian systems. The baculovirus infects the host insect cells, replicates its genome through numerous cycles, and then produces large amounts of polyhedron crystals. The polyhedron gene can be replaced with an oxidation resistant TM analog gene. The polyhedron promoter will then make large amounts of analog protein following infection of the culture host cell and replication of the baculovirus genome. The non-secreted gene product is harvested from the host 3–7 days post infection. Alternatively, the oxidation resistant TM analog protein may be secreted from the cells if appropriate signal sequences are present on the protein.

The host cells are competent or rendered competent for transfection by various means. There are several well-known methods of introducing DNA into animal cells. These include: calcium phosphate precipitation, DEAE-dextran technique, fusion of the recipient cells with bacterial protoplasts containing the DNA, treatment of the recipient cells with liposomes containing the DNA, electroporation and microinjection of the DNA directly into the cells. See, B. Perbal, "*Practical Guide to Molecular Cloning,*" 2nd edition, John Wiley & Sons, New York and Wigler, et al. (1987) *Cell*, 16:777–785.

Culturing Cells

It is preferred that the host cell is capable of rapid cell culture and able to appropriately glycosylate expressed gene products. Cells known to be suitable for dense growth in tissue culture are particularly desirable and a variety of invertebrate or vertebrate cells have been employed in the art, both normal and transformed cell lines.

The transfected cells are grown up by means well known in the art. For examples, see Biochemical Methods in *Cell Culture and Virology*, Kuchler, R. J., Dowden, Hutchinson and Ross, Inc. (1977). The expression products are harvested from the cell medium in those systems where the protein is secreted from the host cell or from the cell suspension after disruption of the host cell system by, e.g., mechanical or enzymatic means, which are well known in the art.

Purification of Soluble Oxidation Resistant TM Analogs

The present invention provides soluble oxidation resistant TM analogs which are secreted by cultured recombinant eukaryotic cells. The analogs are produced in serum-free or serum supplemented media and are secreted intact. If prokaryotic cells are used, the oxidation resistant TM analogs may be deposited intracellularly. The analogs may be glycosylated or non-glycosylated. Following the growth of the recombinant cells and concomitant secretion of oxidation resistant TM analogs into the culture media, this "conditioned media" is harvested. The conditioned media is then clarified by centrifugation or filtration to remove cells and cell debris. The proteins contained in the clarified media are concentrated by adsorption to any suitable resin such as, for example, Q Sepharose or metal chelators, or by use of ammonium sulfate fractionation, polyethylene glycol precipitation, or by ultrafiltration. Other means known in the art may be equally suitable. Further purification of the soluble oxidation resistant TM analogs can be accomplished in the manner described in Galvin, J. B., et al. (1987) *J. Biol. Chem.*, 262:2199–2205 and Salem, H.H. et al. (1984) *J. Biol. Chem.*, 259:12246–12251 and in the manner described in the embodiment disclosed herein. The purification of oxidation resistant TM analogs secreted by cultured cells may require the additional use of, for example, affinity chromatography, ion exchange chromatography, sizing chromatography or other protein purification techniques.

Recombinant oxidation resistant TM analogs may be produced in multiple conformational forms which are detectable under nonreducing chromatographic conditions. Removal of those species having a low specific activity is desirable and is achieved by a variety of chromatographic techniques including anion exchange or size exclusion chromatography.

Recombinant oxidation resistant TM analogs may be concentrated by pressure dialysis and buffer exchanged directly into volatile buffers (e.g., N-ethylmorpholine (NEM), ammonium bicarbonate, ammonium acetate, and pyridine acetate). In addition, samples can be directly freeze-dried from such volatile buffers resulting in a stable protein powder devoid of salt and detergents. In addition, freeze-dried samples of recombinant analogs can be efficiently resolubilized before use in buffers compatible with infusion (e.g., phosphate buffered saline). Other suitable buffers might include hydrochloride, hydrobromide, sulphate acetate, benzoate, malate, citrate, glycine, glutamate, and aspartate.

Formulation and Use of Thrombomodulin Analogs

Soluble oxidation resistant TM analogs described herein may be prepared in a lyophilized or liquid formulation. The material is to be provided in a concentration suitable for pharmaceutical use as either an injectable or intravenous preparation.

These compounds can be administered alone or as mixtures with other physiologically acceptable active materials, such as one-chain t-PA, or inactive materials, or with suitable carriers such as, for example, water or normal saline. These compounds can be administered parenterally, for example, by injection. Injection can be subcutaneous, intravenous or intramuscular. These compounds are administered in pharmaceutically effective amounts and often as pharmaceutically acceptable salts, such as acid addition salts. Such salts can include, e.g., hydrochloride, hydrobromide, phosphate, sulphate, acetate, benzoate, malate, citrate, glycine, glutamate, and aspartate, among others. The analogs described herein may display enhanced in vivo activity by incorporation into micelles. Methods for incorporation into ionic detergent micelles or phospholipid micelles are known.

An antithrombotic agent can be prepared using the soluble oxidation resistant TM analogs described herein and can consist of a completely purified analog alone or in combination with a thrombolytic agent as described above. Compounds of the present invention which are shown to have the above recited physiological effects can find use in numerous therapeutic applications such as, for example, the inhibition of blood clot formation. Thus, these compounds can find use as therapeutic agents in the treatment of various circulatory disorders, such as, for example, coronary or pulmonary embolism, strokes, as well as the prevention of reocclusion following thrombolytic therapy, and these compounds have utility in the cessation of further enlargement of a clot during an infarction incident. Further, the compounds disclosed can be useful for treatment of systemic coagulation disorders such as disseminated intravascular coagulation (DIC), which is often associated with septicemia, certain cancers and toxemia of pregnancy.

These compounds can be administered to mammals for veterinary use, such as with domestic animals, and for clinical use in humans in a manner similar to other therapeutic agents, that is, in a physiologically acceptable carrier. In general, the administration dosage will range from about 0.0001 to 100 mg/kg, and more usually 0.001 to 0.1 mg/kg of the host body weight. These dosages can be administered by constant infusion over an extended period of time, until a desired circulating level has been attained, or preferably as a bolus injection.

Multifunctional Proteins

The mutant oxidation resistant TM analog proteins may have amino acids at either their N-terminal or C-terminal ends that do not correspond to amino acids from the native thrombomodulin sequence. These terminal amino acids may be the result of post-translational processing and originate from a heterologous signal peptide. Alternatively, the non-thrombomodulin amino acids may correspond to heterologous protein sequences that impart biological characteristics to the mutant TM analog not normally associated with native thrombomodulin. These multifunctional proteins are composed of a first functional component that is associated with an activity of native thrombomodulin, thrombin binding or protein C activation cofactor activity, for example, and a second functional component that is heterologous, ie, is a biological activity associated with some other protein or proteins. The second functional component may effect localization of the multifunctional oxidation resistant TM analog so as to modify its affinity for specific tissue structures occurring in vivo, such as cell surfaces or fibrin clots. The second functional component may alter the circulating half-life of the multifunctional protein. In a preferred embodiment, the second functional component provides an additional biological activity such as a proteolytic activity. A preferred proteolytic activity is the enzymatic cleavage of plasminogen to plasmin. The heterologous protein sequence conferring proteolytic activity to the multifunctional TM analog is preferably derived from tissue plasminogen activator (t-PA) or pro-urokinase. A particularly preferred embodiment includes amino acids 4–530 of human t-PA. The second functional component may be joined to the oxidation resistant TM analog at either the C-terminal or N-terminal. (See FIG. 1B).

In an additional embodiment, the multifunctional protein may be created by chemical conjugation rather than as fusion protein. Ruger, et al, (1987) *Proc. Natl. Acad. Sci. USA* 84:7659–7662 and Smith and Cassels, (1988) *Fibrinolysis* 2:189–195 have described chemical linkages between t-PA and other molecules. The methods used to make chemical conjugates often involve the use of oxidants. Thus, an oxidation resistant TM analog is particularly preferred in this embodiment. These molecules have an altered affinity for cell surfaces or enhanced affinity for fibrin.

The multifunctional oxidation resistant TM analogs containing additional domains that impart fibrinolytic activity in combination with antithrombotic activity will provide additional and superior utilities over currently available compounds. Fibrinolytic activity (the ability to lyse a fibrin clot) can be evaluated in vitro using Zonal clearing on plasminogen-enriched fibrin plates as described by Haverketet and Brakman, (1975) *Prog. in Chem. Fibrin. Thromb.* 1:15–159. These multifunctional proteins direct the multifunctional oxidation resistant TM analog to the site of the fibrin clot. The fibrinolytic activity conferred upon the compound by the heterologous domain provides a superior thrombolytic agent. As the clot is lysed by the fibrinolytic action of the, for example, t-PA domains(s), the TM domain(s) are inherently located precisely where needed to bind thrombin and inhibit any further growth of the clot matrix. This thrombin may be either newly generated by the coagulation pathway or released from the dissolving clot. The antithrombotic activity of the multifunctional peptide will not be compromised by the presence of active oxygen intermediates, such as are common during reperfusion. The therapeutically effective dose of the multifunctional protein will be less than the doses of each molecule administered individually, reducing any concerns about the broader systemic action of either the TM analog or the t-PA and any consequential undesirable side effects.

A preferred source of the t-PA gene can be obtained by isolating the t-PA gene from an *E. coli* culture (strain MH-1) on deposit with American Type Culture Collection (ATCC) in Bethesda, Maryland having Accession No. 67,443. Standard cloning techniques are sufficient to obtain the t-PA plasmid and to insert heterologous domains, as desired, into genes encoding TM analogs.

Coating of Biomaterials with Oxidation Resistant TM Analogs

The use of altered prosthetic endovascular or cardiovascular devices anywhere in the circulation system result in the formation of thrombus, a blood-derived mass as a pathological consequence of activating hemostatic mechanisms under variable flow conditions. Typically, thrombogenesis in association with prosthetic endovascular or cardiovascular devices includes the following sequence:
(a) exposure of the surface to circulating blood;
(b) platelet adherence, aggregation and release of platelet components;
(c) thrombin generation and fibrin formation;
(d) thrombin dissolution which requires plasmin generation and fibrinolysis.

In general, when blood contacts an artificial surface, the surface will rapidly acquire a layer of absorbed plasma proteins which will mediate an inflammatory response with the concomitant generation of active oxygen species ultimately resulting in thrombosis. This series of events also follows when blood is circulated through an extracorporeal device, such as a heart/lung machine.

It has been desirable to introduce various coatings onto the polymeric surfaces of such blood-contacting devices to promote thromboresistance. Oxidation resistant thrombomodulin represents a new class of molecule suitable for creating a thromboresistant surface. It is especially suitable as such a surface since it has no known inhibitors and will be available to function in this capacity for extended periods of time.

The oxidation resistant TM analogs described herein are particularly advantageous for this purpose as they do not lose activity in the face of inflammation and some of the analogs are closely related to the protein fragment which is derived when full length TM is digested with porcine pancreatic elastase. The long-term stability of immobilized proteins is of paramount importance. Thus, the smaller, proteolytically and oxidation resistant TM analog is more advantageous than the full length molecule which can be proteolysed by enzymes in the blood, resulting in the potential loss of active component from the biomaterial surface as well as being rendered inactive by oxidants. The stability of the immobilized protein is also significantly enhanced by mutations that render it immune to oxidation, which destroys its antithrombotic utility. The oxidation resistant TM analogs will be particularly preferable over the use of the full length molecule, inter alia, during periods of physiological stress, e.g., inflammation, where potent white cell proteases, including leukocyte elastase, and active oxygen intermediates have access to the biomaterial surface.

The oxidation resistant TM analogs may be used to coat polymers used in a wide variety of biological applications including, but not limited to, arteriovenous shunts, intravascular shunts (eg., umbilical, angiographic), vascular grafts, heart valves, artificial joints, pacemakers, left ventricle assist devices, and the like.

The oxidation resistant TM analogs are bonded to a biocompatible polymer. Biocompatible polymers may be any suitable polymeric biomaterial or combination thereof known and used in the art for biological application such as polyurethanes, silicone elastomers, hydrogels (e.g., poly(hydroxyethyl methacrylate), polyesters, polyethers, polyvinyl alcohol, and the like.

The oxidation resistant TM analog may be bonded to coat the polymer material following activation of the biopolymer. Activation methods are known in the art and may utilize amino, carboxyl, hydroxyl or sulfhydryl functions on the compound to be coated. Activation may be achieved through a variety of known mono- and/or bi-functional reagents, including, but not limited to, glutaraldehyde, carbodiimide activated COOH, isocyanate, cyanuric acid, or hydrosuccinimide esters. Spacer arms bound to the polymers and known in the art, may optionally be used. Modifications made to the primary sequence or to the chemical structure of the amino acids of the peptides of this invention are referred to as means for binding the peptide to the biocompatible polymer. Such means include spacer arms such as polylysine moieties, ligand/antiligand binding pairs such as antibodies/antigens and biotin/avidin.

Once the biocompatible polymer has been coated, it may be implanted in a mammal as necessary according to the teaching in the art for the procedure at hand or used in any device that contacts blood where the blood must remain anticoagulated.

The following examples are offered by way of illustration and not by way of limitation.

EXAMPLES

Example 1

Construction of Genes for Oxidation Resistant Analogs

1. Isolation of TM analog sequences

Genes for producing recombinant thrombomodulin analog peptides were isolated as described in copending applications U.S. Ser. No. 312,141 filed Feb. 17, 1989, U.S. Ser. No. 345,372 filed Apr. 28, 1989, U.S. Ser. No. 406,941 filed Sep. 13, 1989 and PCT Ser. No. 90/00955 filed Feb. 16, 1990, each herein incorporated by reference. Briefly, human DNA was used to isolate a gene encoding the 6 EGF-like domains of thrombomodulin corresponding to amino acids 227–462 as well as other portions of the thrombomodulin peptide. (See Table 1). This DNA was isolated from fetal liver according to the method of Blin, N and DW Stafford, (1976) Nucleic Acids Res. 3:2302. The DNA was then used as a template in a polymerase chain reaction with synthetically derived primers selected to embrace the desired regions (See Tables 3 & 4, FIGS. 1A and 2).

a. Isolation of genes encoding amino acids 227–462

Figure 2:
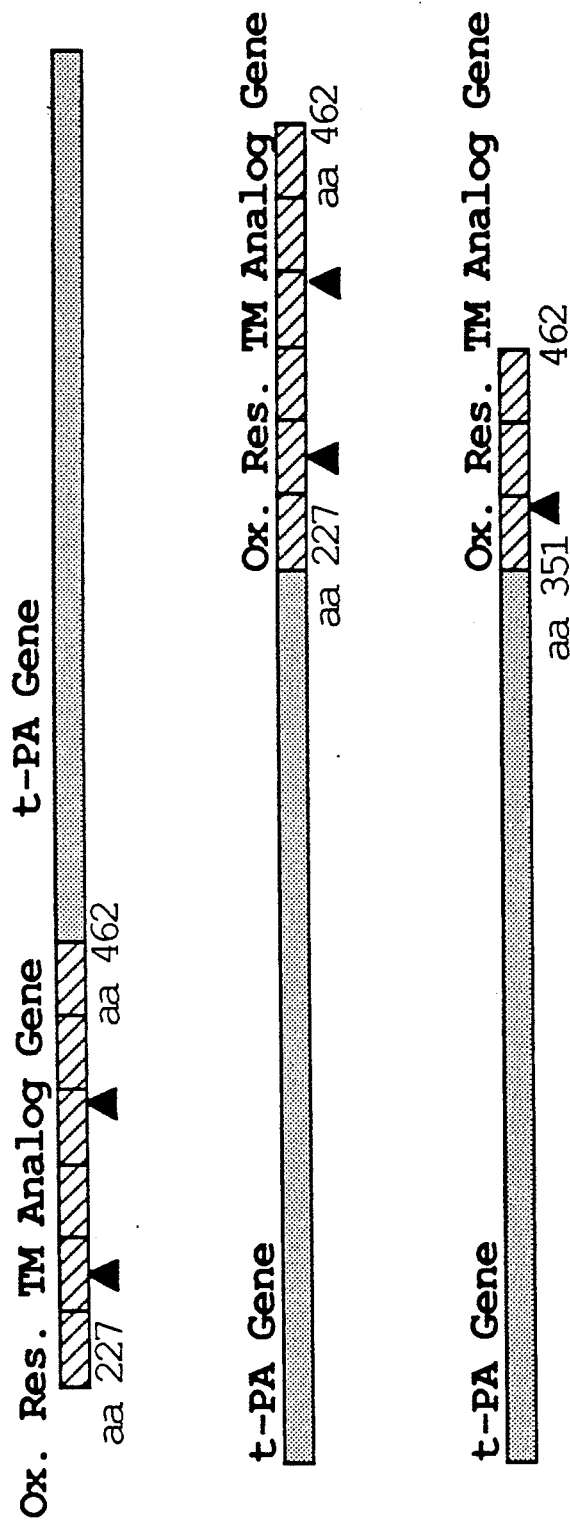
FIG. 2 depicts two of the primers used in the PCR reaction to create wild-type (non-mutant) gene sequences for the TM analogs described herein and the cloning plasmid pUCpcrTM7.

The following steps provide a means to obtain a DNA insert encoding amino acids (aa) 227–462 and uses primers #1033 and #1034 (See FIG. 2). It is understood that by modifying the procedures set forth below by using alternative primers, other soluble TM analogs can be obtained.

The sequence of the #1033 and #1034 primers correspond to the 5' and 3' ends of the desired domain; but they have been modified so that they contain a BamHI site. A termination codon (TGA) was introduced following base 1586. The polymerase chain reaction was run under the conditions described by Saiki, et al, (1988) Science 320:1350-1354, except that the initial temperature of annealing was 37° C. After 10 cycles, the annealing temperature was raised to 45° C. for the remaining 30 cycles. An aliquot of the reaction products was separated on a 5% polyacrylamide gel and visualized by ethidium bromide staining. A band of the predicted size (700 bp) could clearly be seen. Alternatively one can sequence this band or hybridize it to an internal probe to confirm its identity.

b. Isolation of genes encoding other regions of thrombomodulin

The polymerase chain reaction as herein described was used in the same manner to isolated additional fragments of thrombomodulin corresponding to the regions listed in Table 3, some of which are shown schematically in FIG. 1A. In particular, these regions embrace one or more of the EGF-like domains and the O-linked glycosylation domain. The sequences of the primers selected to produce the desired regions are shown in Table 4.

c. Cloning plasmids containing the thrombomodulin analog genes i. pUC19pcrTM7

The remainder of the polymerase chain reaction mixture described in part a.) above was restricted with BamHI, separated on a 5% polyacrylamide gel, and the 700 bp band was excised and eluted. It was ligated to pUC19 that had been restricted with BamHI and the new plasmid was transformed into E. coli strain DH5-alpha. Recombinant colonies were selected on a medium containing ampicillin and 5-bromo-4-chloro-3-indolyl-β-D-galactoside. White colonies were picked onto a grid and hybridized by the Grunstein-Hogness technique with a synthetically derived gene corresponding to aa 283-352 of thrombomodulin that had been cut out of a cloning plasmid (pTM2.1) with EcoRI and HindIII before labelling with 32P by random priming (Boehringer Mannheim).

After exposing the filters to X-ray film, the one colony that hybridized to the pTM2.1 probe (pUC19pcrTM7, See FIG. 2) was selected and a culture grown up. DNA was extracted and analyzed by restriction with either BamHI or BglII to confirm the presence of an insert with the correct restriction map. The excised insert was also transferred to nitrocellulose and analyzed by hybridization with labelled pTM2.1. Both methods confirmed that the 700 bp insert contained the coding sequence for the 6 EGF-like domains of thrombomodulin. The insert was sequenced to verify that no mutations had been inadvertently introduced during the PCR.

ii. Cloning plasmids containing other thrombomodulin analog genes

Other cloning plasmids, such as pTM309 and pTM323 were constructed using methods similar to those described in to those described in (i.). Plasmid pTM309 contains amino acids 350-462 of native thrombomodulin (EGF-like domains 4,5&6) and pTM323 contains amino acids 227-497 (EGF-like domains 1-6 +the O-linked glycosylation domain).

Additional plasmids were constructed that contain other thrombomodulin analog gene sequences. (See Table 3).

d. Construction of AcNPV Transfer Vectors

The transfer vectors described below are also described in copending application U.S. Ser. No. 345,372 filed Apr. 28, 1989 herein incorporated by reference.

i. Vectors with the Hypodermin A signal sequence: pHY1 and pSC716

Two oligomers, COD#1198 and COD#1199 were synthesized, see Table 4. These oligomers contain the Hypodermin A signal sequence, a translation initiation codon, a BglII cloning site, a BamHI 5' overhand and a Kpnl 3' overhang. COD#1198 and COD#1199 were annealed and cloned into pSC654, a pUC19 derivative, creating pHY1. The sequence of the hypodermin A signal peptide is shown in Table 2.

Plasmid pHY1 was restricted with BamHI and EcoRI, releasing the hypodermin A signal sequence. This sequence was then ligated to pSC714 to create the vector pSC716. Plasmid pSC714 is a derivative of pVL1393, obtained from Summers, et al. The only difference between the two is that in pSC714, one of the BglII sites has been destroyed.

ii. Construction of pHY101

The BamHI fragment from pUC19pcrTM7 was cloned into the BglII site of pHY1 and the orientation was chosen such that the hypodermin A signal sequence was adjacent to amino acid 227. This plasmid is pHY101.

iii. Construction of the AcNPV transfer vector pTMHY101

Plasmid pHY101 was treated with BamHI/EcoRI which releases the Hypodermin A signal sequence linked to the TM analog coding sequence. Shuttle vector pVL1393 contains a partially deleted AcNPV polyhedrin gene and unique BamHI and EcoRI cloning sites. The BamHI/EcoRI fragment from pHY101 was inserted downstream of the polyhedrin promoter, thus creating a plasmid, pTMHY101, in which the hybrid gene was under the control of the polyhedrin promoter. This plasmid is shown in FIG. 4.

iv. Construction of other ACNPV transfer vectors

Transfer plasmids containing other TM analog gene sequences were constructed using a strategy similar to that outlined above. Fragments from the cloning plasmids described above were cloned into pSC716 in frame so that the TM analog gene sequence was fused to the hypodermin A signal sequence. The TM gene sequences are listed in Table 3 and shown schematically in FIG. 1A.

2. Site-directed Mutagenesis

Figure 3:
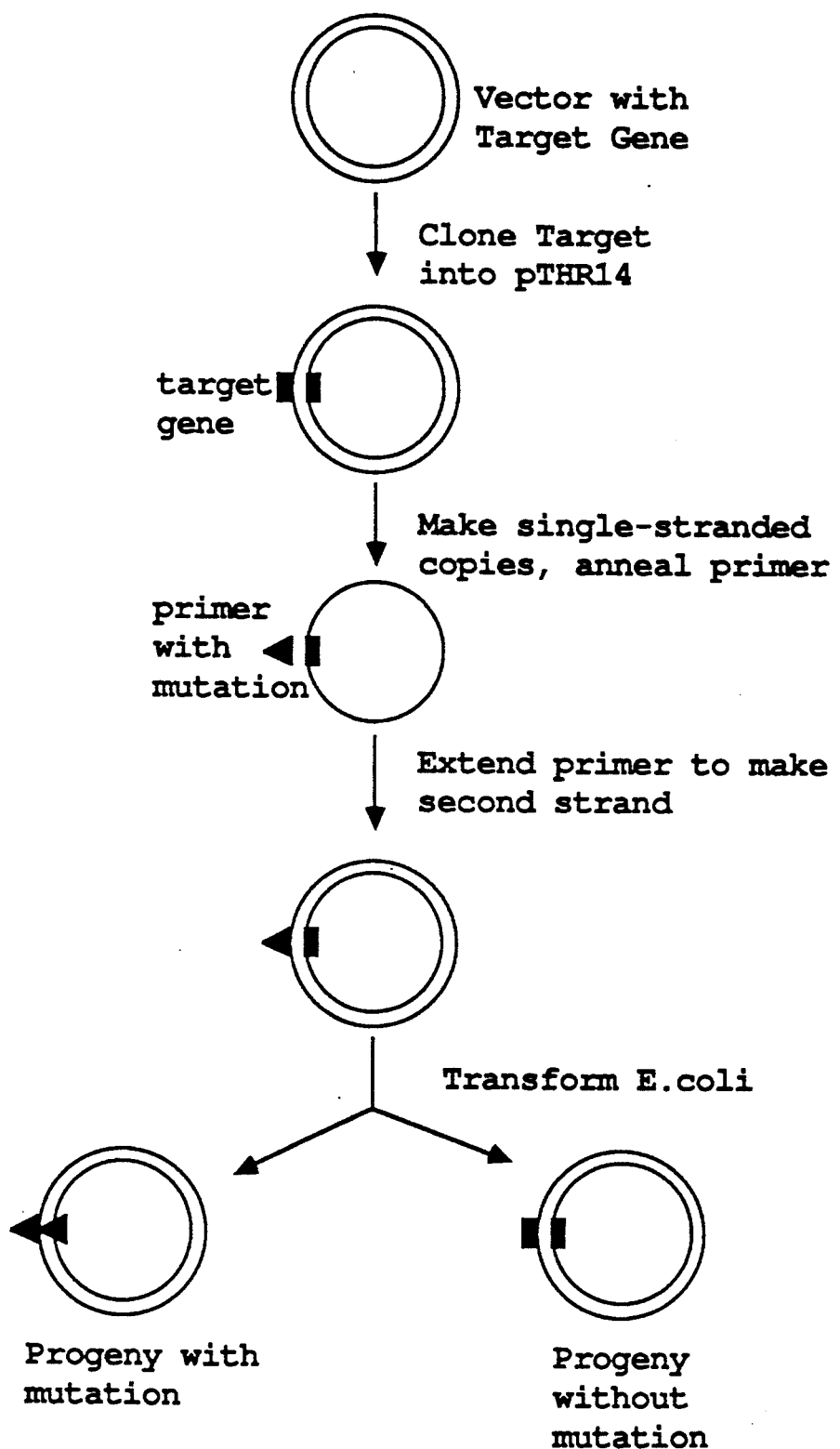
FIG. 3 schematically illustrates the method of site directed mutagenesis used to create the oxidation resistant TM analogs described by this invention.

The 6 EGF-like domains region of native thrombomodulin has two methionine residues, one at position 291 and one at position 388. (See Table 1). Site-directed in vitro mutagenesis was used to convert either or both of these methionines to other amino acids. Site-directed mutagenesis uses a synthetic DNA sequence containing a desired nucleotide substitution, insertion or deletion to specifically alter the nucleotide sequence of a single-stranded template DNA. Hybridization of this synthetic DNA to the template and subsequent primer extension produces a heteroduplex DNA capable of cell transformation to yield the desired mutation. A diagram depicting this process is shown in FIG. 3.

a. Plasmid pTHR14

A plasmid for making single stranded DNA copies was constructed by ligating the F1 origin of replication contained on an AseI-ScaI fragment into an insect cell transfer vector, pTMHY101, previously digested with NdeI and ScaI. Plasmid pTMHY101 contains a gene sequence that produces a peptide corresponding to the 6 EGF-like domains of thrombomodulin, amino acids 227–462. The numbers 227–462 refer to the amino acids corresponding to the native thrombomodulin sequence (Table 1). Amino acids 227–462 comprise the 6 EGF-like domains. pTMHY101 is fully described in copending application U.S. Ser. No. 345,372 and is shown diagrammatically in FIG. 4.

b. Site-directed mutation

Specific mutagenizing oligonucleotide primers were synthesized and used with the MUTATOR TM —DNA Polymerase III Site-directed Mutagenesis Kit (Catalogue #200500, Stratagene, La Jolla, CA), except as otherwise noted to prime second strand synthesis and create thrombomodulin analog genes with either one or both of the methionines changed to a non-oxidizable amino acid. Primers directing conversion to the preferred amino acids leucine, glutamine or alanine are shown in Table 5. Also included in these primers are substitutions in the nucleotide sequence that add a unique restriction enzyme site useful as a diagnostic for successful mutagenesis but which do not necessarily change the corresponding amino acid sequence. The nucleotide substitutions are underlined in the primers shown in Table 5. For example, in plasmid pTHR28 the methionine at position 388 in the native thrombomodulin protein was replaced with leucine, and in the process a unique PvuII site was introduced. It is understood that other substitute non-oxidizable amino acids would be equally useful in this invention.

Purified single-stranded DNA templates were prepared using the procedure described by Bio-Rad (Muta-Gene Phagemid in vitro Mutagnesis, Instruction Manual, Cat. no. 170-3576, pgs 33-34) although other procedures known in the art would be equally suitable.

The 5' terminus of each mutagenizing primer was phosphorylated by incubating 0.5 ng/ul of primer in a solution containing 2 mM rATP, 0.4 U/ul polynucleotide kinase in annealing buffer (20 mM Tris-HCl pH 7.5, 8 mM MgCl2 and 40 mM NaCl) at 37° C. for 30 minutes. The reaction was heat inactivated by incubating the mixture at 65° C. for 15 minutes. Phosphorylation increases the rate of successful mutation. The phosphorylated primer was annealed to the single-stranded template by heating 100 ng of template and 2.5 ng of primer in 25 ul of annealing buffer to 65° C. for 5 minutes then allowing the mixture to cool and anneal at room temperature for 10 minutes. Double stranded DNA was made by primer extension essentially as described by Tsurushit, N., et al, (1988) *Gene* 62:135-139 and O'Donnell, M.E., et al, (1985) *J. Biol. Chem.* 260:12875-12883. Briefly, the template/primer mixture was diluted (1:1) with 10% annealing buffer plus 80 ug/ml bovine serum albumin, 2.5 mM dithiothreitol, 0.25 mM mixed dNTPs, 2 mM rATP and 1% glycerol plus 1 ug of single-stranded DNA binding protein. The reaction was incubated for 5 minutes at room temperature to allow the binding protein to coat the single-strand DNA template. DNA polymerase III holoenzyme (*E. coli*, 1.7 ul of 50 U solution) was added, and the reaction was incubated at 30° C. for 10 minutes. T4 DNA ligase was added (0.5 ul, 2 Weiss units) and the reaction was further incubated for 5 minutes at 30° C. This mixture was used to transform *E. coli* and properly mutated clones were selected by restriction digest pattern. Table 3 lists the new plasmids created from pTMHY101 along with the amino acid substitutions made in each.

3. Site-directed Mutagenesis of Other Gene Sequences

Using the method outline above, similar amino acid substitutions are made in the TM analog gene sequences listed in Table 3.

Example 2

Production of Oxidation Resistant TM Analog Proteins

Oxidation resistant proteins were produced using an *Autographa california* nuclear polyhedrosis virus (AcNPV) system in insect cells (*Spodoptera frugiperda* (Sf9)). In this system, the wild type AcNPV polyhedrin gene is replaced with foreign gene sequences by homologous recombination.

1. Production of pure phage stocks

Cell transfection was done using a calcium phosphate precipitation technique modified for insect cells according to Summers and Smith. Briefly, a T25 flask was seeded with $2\times10^6$ Sf9 cells, and the cells were allowed to attach for one hour at room temperature. Two ugs of transfer vector, for example pTHR28, and 1 ug of AcNPV DNA were coprecipitated in calcium phosphate and incubated with the cells for 4 hours. The cells were rinsed and re-fed with growth media, then placed in a 28° C. incubator for 3–4 days. During this incubation, the cells produce both recombinant and non-recombinant virus which accumulate in the growth media. This media, containing a mixed viral stock, was assayed for the presence of protein C cofactor activity (see below).

Recombinant viruses were detected by plaque assay. The transfection stocks were diluted ($10-^4$, $10-^5$, and $10-^6$) and plated 4–7 days post-transfection. Occlusion negative (recombinant) plaques were picked 7 days after plating and replated ($10-^1$, $10-^2$, and $10^3-$ dilution). After another 7 days, the plates showed 100% pure occlusion negative recombinant plaques. A single pfu from each was selected for production. A high titer viral stock was grown by infecting 5 mls of Sf9 cells ($1\times10^6$/ml in Excell 400 medium (JR Scientific)) with a single pfu, growing for 4–5 days. A portion of this stock was then diluted 1:50–1:100 into Sf9 cells grown to mid-log phase to produce a protein stock.

2. Production of recombinant protein

T25 flasks were seeded at a density of 2×106 Sf9 cells in 5 ml TMN-FH media plus 10% FBS or Excell 400, then infected with an isolated recombinant plaque. Viral stocks were collected after three days. Flasks (30–100 ml shaker flasks or 100–300 ml spinner flasks) were seeded with cells (1–1.8×106/ml) and infected with aliquots of the viral stock equal to 1/50th to 1/100th of the final volume. The infected cell cultures were grown for four days before harvesting the conditioned media containing recombinant oxidation resistant TM analog protein.

Example 3

Assays for Thrombomodulin Activity

The retention of thrombomodulin activity by the mutant oxidation resistant TM analogs was initially assessed by evaluating the ability of the new peptide to act as a cofactor for the thrombin mediated activation of protein C.

1. Materials

Rabbit thrombomodulin, hirudin and human protein C were supplied by American Diagnostica. Human thrombin is available from a variety of noncommercial and commercial sources. Bovine thrombin was purchased from Mile Labs, Dallas, Texas. D-valyl-L-leucyl-L-arginine-p-nitroanilide (S-2266) and D-Phe-Pip-Arg-p-nitroanilide (S-2238) were purchased from Kabi Diagnostica. Bovine serum albumin (fraction V) and citrated human plasma were purchased from Sigma Chemicals. Microtiter Plates were supplied by Corning (#25861-96). All other reagents were of the highest grade available.

2. Assay Methods

The protein C activation assay (chromogenic) was performed by mixing 20 ul each of the following proteins in a microtiter plate: thrombomodulin sample (unknown or standard), thrombin (3 nM), and protein C (0.15 to 1.5 uM). The assay diluent for each protein was 20 mM Tris-HCl, 0.1M NaCl, 2.5 mM CaCl2, 5 mg/ml BSA, pH 7.4. The wells were incubated for 0.5 to 2 hours at 37° C., after which protein C activation was terminated by the addition of 20 ul of hirudin (0.16 unit/ul, 370 nM) in assay diluent and incubated for an additional 10 minutes.

The amount of activated protein C formed was detected by adding 100 ul of 1.0 mM S-2266 (in assay diluent), and continuing to incubate the plate at 37° C. The absorbance at 405 nm in each well was read every 10 seconds for 30 minutes using a Molecular Devices plate reader. The absorbance data was stored, and the change in absorbance per second (slope) in each well was calculated. The change in absorbance per second is proportional to pmole/ml of activated protein C. This ratio was determined empirically using varying concentrations of totally activated protein C. Samples containing 100% activated protein C were generated by mixing protein C at 0 to 1.5 uM with 60 nM native rabbit thrombomodulin and 30 nM thrombin, incubating for 0 to 4 hours, adding hirudin and measuring conversion of S-2266 as above. Conditions under which 100% of the protein C was activated were defined as those in which the S-2266 conversion (A405/sec) reached a plateau.

A unit of activity is defined as 1 pmole of activated protein C generated per ml per minute under the reagent conditions defined above. Alternatively, activity values reported were calculated using rabbit thrombomodulin or a wild-type (non-mutant) TM analog, 6h/227–462 as a standard. By using amino acid analysis to deduce protein mass, it has been determined that 1 nmole of wild-type TM analog (6h/227–462) has activity equivalent to 1 nmole of rabbit native thrombomodulin.

3. Activity after exposure to oxidants

Chloramine-T (N-Chloro-p-toluenesulfonamide sodium salt, Sigma) was used to specifically test the resistance of the mutant TM analog peptides to oxidation. Transfection culture supernatant (1 ml) containing a peptide encoded by a mutant TM gene sequence or pTMHY101 (wild-type, aa 227–462) desalted into 1.5 ml of 0.2% N-ethylmorpholine (NEM), pH 7.0, 0.008% Tween 80 on a NAP-10 column (LKB/Pharmacia) and then lyophilzed and resuspended in 100 ul of the above buffer. The sample was divided equally and either 5 ul of water (control) of 5 ul of 0.1M chloramine-t (final conc.=9.1 nM) was added. The samples were incubated at room temperature for 20 minutes, then passed over the NAP-5 column to remove any oxidant. The desalting buffer used was protein C assay diluent. The results shown below demonstrated that the mutant peptide retained all of its activity after being exposed to chloramine-T whereas the wild type peptide was substantially inactivated. Activity is reported in nanomolar equivalents to native thrombomodulin.

| Peptide | Activity (nM) | % Activity Recovered |
|---|---|---|
| wild type (−) CHT | 6.77 | — |
| wild type (+) CHT | 0.46 | 7 |
| Met$_{388}$→Leu (−) CHT | 17.41 | — |
| Met$_{388}$→Leu (+) CHT | 17.83 | 102 |
| Met$_{388}$→Gln (−) CHT | 0.71 | — |
| Met$_{388}$→Gln (+) CHT | 0.72 | 101 |
| Met$_{388}$→Leu:Met$_{291}$→Leu (−) CHT | 0.97 | — |
| Met$_{388}$→Leu:Met$_{291}$→Leu (+) CHT | 1.07 | 110 |

No loss in protein mass was detected in any of the samples. Other mutant TM analogs tested showed similar results.

Example 4

Purification and Specific Activity

The oxidation resistant TM analogs were purified from conditioned media by removal of cell debris, followed by five chromatography steps: 1) Q Sepharaose, 2) thrombin affinity, 3) gel filtration, 4) anion exchange, and 5) a second gel filtration step. The gel filtration steps effect an exchange of buffers. All chromatography steps were performed at 4° C.

1. Materials

Some of the chromatographic resins were purchased from commercial sources. Q Sepharose and Sephadex G25 was purchased from Sigma (St. Louis, MO), and Mono Q 5/5Tm from Pharmacia LKB (Piscataway, NJ).

DFP-thrombin agarose was prepared approximately as follows: 360 mg of bovine thrombin in 100 ml of 20 mM Na phosphate, pH 7.5 was added to approximately 100 ml of a 50% Affigel 10 resin slurry and mixed overnight at 4° C. The Affigel 10 was prepared for use as described by the manufacturer and equilibrated with the load buffer. Residual active esters were blocked by the addition of 100 ml of 0.1M glycline (pH 5.6) for one hour at 4° C. The gel was then equilibrated with 30 mM Tris-HCl, 2M NaCl, pH 7.5, and 20 µl of DFP was added to give a final concentration of about 1 mM DFP. After 16 hrs of mixing at 4° C. an additional 6 µl of DFP was added and mixing continued for 4 additional hours. The resin was then washed with 20 mM Tris-HCl, 2M NaCl pH 7.5 and stored at 4° C.

Thrombin activity was measured using the Kabi S-2238 substrate and indicated that >86% of the thrombin was removed from the solution, and presumably coupled to the resin, giving a final concentration of about 6 mg of thrombin per ml of resin. The enzymatic activity of the DFP treated resin was <1% of the starting activity.

2. Production of pure Met388→Leu peptide

Conditioned media was harvested and clarified by centrifugation at 1400xg for 10 minutes. the pH was adjusted from about 6.0 to about 5.2 with glacial acetic acid. The adjusted media was then loaded onto a column of Q Sepharose resin. The column had previously been equilibrated with about four column volumes of wash buffer 1 (117 mM Na acetate, 0.02% NaN$_3$ pH 5.0). After loading, the column was washed with wash buffer 1 followed by wash buffer 2 (25 mM Na acetate, 0.1M NaCl pH 5.0) then the oxidation resistant TM analog was eluted with wash buffer 2 containing 0.3M NaCl, pH 5.0.

Column fractions containing activity as measured in the protein C activation assay (see above) were pooled, then diluted with of 0.3M NaCl, 20 mM Tris-HCl, 0.5 mM $CaCl_2$, 0.02% $NaN_3$, pH 7.5. The pH of the diluate was measured and adjusted to about 7.5 with NaOH. The ionic strength of the pool was about the ioinic strength of a solution of 0.3M NaCl. This adjusted pool was loaded overnight by gravity onto a thrombin agarose column pre-equilibrated with the same buffer used to dilute the conditioned media. The column was washed with diluent buffer, and the TM analog was removed from the matrix with 1.5M GuHCl, 2.0M NaCl, 20 mM Tris HCl, 1 mM Na EDTA, 0.02% $NaN_3$, pH 7.5.

The substantially pure, active oxidation resistant TM analog was applied to a Sephadex G25 column and recovered in 0.2% N-ethylmorpholine acetate (NEM) pH 7.0. This step removes GuHCl and NaCl.

Oxidation resistant TM analog collected from the Sephadex G25 column was applied to a Mono Q column (Pharmacia, 10 micron particles, quarternary amine) pre-equilibrated with 0.2% N-ethylmorpholine (NEM). pH7.0. After washing with this buffer the various forms were separated using a gradient of 0 to 0.4M NaCl. Samples of each fraction were evaluated on an SDS-PAGE gel under non-reducing conditions. SDS Polyacrylamide Gel Electrophoresis was performed by the method of Laemmli using 3.3% acrylamide in the stacking and 12.5% acrylamide in the running gel. Nonreduced samples were diluted in Laemmli sampled solubilization buffer (50 mM Tris-HCl, pH 6.8, 25% glycerol, 2% SDS, and 0.01% bromphenol blue) and loaded directly onto the gel. Pharmacia LMW Calibration Kit protein standards were used for MW markers, and the gels were silver stained. Under these conditions only a single band is visible with silver staining.

Fractions containing peptides with like mobilities were pooled and then assayed for total protein content and for activity in the protein C activation assay. The peak containing the highest specific activity was compared to a peptide fraction containing the wild-type TM analog peptide (native sequence without mutation) that had been purified using the same procedure. The specific activity of the $MET_{388}\rightarrow Leu$ TM analog was 1.93 times (average from 3 types of protein determinations) the specific activity of the wild-type TM analog (803,000 +/−79,000 u/mg vs. 416,000 +/−19,000 u/mg).

4. Retention of Activity Following Exposure to Oxidants

The purified protein ($Met_{388}\rightarrow Leu$) was evaluated for its ability to remain active after exposure to both chloramine-T and hydrogen peroxide. Three aliquots of each of the purified sample proteins (5 ul mutant or wild-type) in 0.2% of NEM pH 7.0 were diluted with 50 ul of protein C assay diluent. The samples received either 5 ul water, 5 ul of 0.1 chloramine-T (CHT) (final conc.=8.33 mM) or 5 ul 30% hydrogen peroxide (final conc.=0.74M). The samples were incubated 20 minutes at room temperature, diluted 200X in protein C assay diluent then assayed for protein C cofactor activity. The results shown in the table below confirm that the mutant TM analog retained activity after exposure to both oxidants.

| Peptide | Activity (nM) | % Activity Recovered |
| --- | --- | --- |
| wild-type (−) CHT | 5100 | 100 |
| wild-type (+) CHT | 860 | 17 |
| wild-type (+) $H_2O_2$ | 1300 | 26 |
| $Met_{388}\rightarrow Leu$ (−) CHT | 3230 | 100 |
| $Met_{388}\rightarrow Leu$ (+) CHT | 3120 | 97 |
| $Met_{388}\rightarrow Leu$ (+) $H_2O_2$ | 3710 | 115 |

Example 5

Therapeutic Application

The soluble oxidation resistant TM analogs will be used to prevent the development of deep venous thrombosis in patients, particularly those undergoing orthopedic surgery such as total hip replacement or repair. Administration of the oxidation resistant TM analog is preferably given prior to surgery when intended as a prophylactic but may also be given to the patient during or following the surgical procedure. Intravenous injection is a convenient route of administration is these patients as they are already receiving various other substances, however, sub-cutaneous or intramuscular administration would be equally effective. The oxidation resistant TM analog will be administered in a pharmaceutically acceptable carrier such as a an acid addition salt, glutamate or aspartate, for example. The dose range will be about 0.0001 to 100 mg/kg of the patient's body weight and more usually 0.001 to 0.1 mg/kg. Proper dosage is monitored by evaluating samples of the patient's serum in the APTT assay. The therapeutically effective dose is given to these patients as a constant infusion over a period of time until a desired level of anticoagulation is reached.

TABLE I

```
GGCAGCGGCGCAGCGGCAAGAAGTGTCTGGGCTGGGACGGACAGGAGAGAGGCTGTGCCGCCATCGGCCGTCCTGTGCCCCTCTGCTCCGG aa  -1 Signal Sequence
                                                                    Met Leu Gly Val Leu Val Leu Gly
CACGGCCCTGTCGCAGTGCCCGCGCTTTCCCCGGCCGCTGCACGCGGCGCGCCTGGGTAACATGCTTGGGGTCCTGGTCCTTGGC
                                                                    T ACGAACCCCAGGACCAGGAACCG
                                                                    T
                                                                    147

↓aa 1 Amino Terminal Domain
Ala Leu Ala Ala Gly Leu Gly Phe Pro Ala Pro Ala Glu Pro Gln Pro Gly Gly Ser Gln Cys Val Glu His Asp Cys Phe
GCGCTGGCCCTGGCCGCCGGCCTGGGGTTCCCCGCACCCGCAGAGCCGCAGCCAGGTGGCAGCCAGTGCGTCGAGCACGACTGCTCC
CGCGACCGGGACCGGCCGGACCCCAAGGGGCGTCTCGGCGTCGGCCCACCGTCGGTCACGCAGCTCGTGCTGACGAAG Ala Leu Tyr Pro Gly Pro Ala Thr Phe Leu Asn Ala Ser Gln Ile Cys Asp Gly Leu Arg Gly His Leu Met Thr Val Arg Ser
GCGCTCTACCCGGGCCCCGCGACCTTCCTCAATGCCAGTCAGATCTGCGACGGACTGCGGGGCCACCTAATGACAGTGCGCTCC
CGCGAGATGGGCCCGGGGCGCTGGAAGGAGTTACGGTCAGTCTAGACGCTGCCTGACGCTGCCCGGTGGATTACTGTCACGCGAGG Ser Val Ala Ala Asp Val Ile Ser Leu Leu Leu Asn Gly Asp Arg Gly Val Gly Arg Arg Gly Pro Leu Trp Ile Gly Leu Gln Leu
TCGGTGGCTGCCGATGTCATTTCCTTGCTACTGAACGGCGACGGCGGCGTTGGCCGCCGGGGCCCTCTGGATCGGCCTGCAGCTG
AGCCACCGACGGCTACAGTAAAGGAACGATGACTTGCCGCTGCCGCCGCAACCGGGCGGCCCGCGGAGACCTAGCCGGACGTCGAC Pro Pro Gly Cys Gly Asp Pro Lys Arg Leu Gly Pro Leu Arg Gly Phe Gln Trp Val Thr Gly Asp Asn Asn Thr Ser Tyr Ser
CCACCCGGCTGCGGGGACCCCAAGCGCCTCGGGCCCCTGCGCGGCTTCCAGTGGGTTACGGGAGACAACAACACCAGCTATAGC
GGTGGGCCGACGCCCCTGGGGTTCGCGGAGCCCGGGACGCGCCGAAGGTCACCCAATGCCCTCTGTTGTTGTGGTCGATATCG Arg Trp Ala Arg Leu Asp Leu Asn Gly Ala Pro Leu Cys Gly Pro Leu Val Ala Val Ser Ala Ala Thr Val Pro
AGGTGGGCACGCTGGACCTCAATGGGGCTCCCCTGTGCGGCCCCGTTGTGCGTCGCTGTCTCCGCTGCTGAGGCCACTGTGCCC
TCCACCCGTGCCGAGCTGGAGTTACCCCGAGGGGAGACGCCGGGCAACACGCAGAGAGGCGACGACTCCGGTGACACGGG Ser Glu Pro Ile Trp Glu Glu Gln Cys Glu Val Lys Ala Asp Gly Phe Leu Cys Glu Phe His Phe Pro Ala Thr Cys Arg
AGCGAGCCGATCTGGGAGGAGCAGCAGTGCGAAGTGCAAGGCCGATGGCTTCCTCTGCGAGTTCCACTTCCCAGCCACCTGCAGG
TCGCTCGGCTAGACCCTCGTCGTCACGCTTCACGTTCACGGCTACCGAAGGAGACGCTCAAGGTGAAGGTGTCGGTGGACGTCC
```

-continued

```
Pro Leu Ala Val Glu Pro Gly Ala Ala Ala Ala Val Ser Ile Thr Tyr Gly Thr Pro Phe Ala Ala Arg Gly Ala Asp Phe
CCACTGGCTGTGGAGCCCGGCGCCGCGGCTGCCGCCGTGCTCGATCACCTAGGCACCCCGTTCGCGGCCCGCGAGCGGACTTC
GGTGACCGACACCTCGGGCCGCGGGCGCCGACGGCGGCAGAGCTAGTGGATGCCGTGGGGCAAGCGCCGGGCGCCTCGCCTGAAG

Gln Ala Leu Pro Val Gly Ser Ser Ala Val Ala Pro Leu Gly Leu Gln Leu Met Cys Thr Ala Pro Pro Gly Ala Val Gln
CAGGCGCTGCCGGTGGGCAGCTCCGCGGTGGCTCCCCTCGGCTTACAGCTAATGTGCACCGCGCCCCGGAGCGGTCCAG
GTCCGCGACGGCCACCGTCGAGGCGCCACCGAGGGGAGCCGAATGTCGATTACACGTGGCGCGGGGCCTCGCCAGGTC aa 227  EGF-1
                                        |=======
Gly His Trp Ala Arg Glu Ala Pro Gly Gly Ala Trp Asp Cys Ser Val Glu Asn Gly Gly Cys Glu His Ala Cys Asn Ala Ile Pro
GGGCACTGGGCCAGGGAGGCCCGGGGCGCTTGGGACTGCAGCGTGGAGAACGGCGGTGCGAGCACGCGTGCAATGCGATCCCT
CCCGTGACCCGGTCCCTCCGCGGCCCGCGAACCCTGACGTCGCACCTCTTGCCGCCACGCTCGTGCGCACGTTACGCTAGGGA
                                                                        879 aa 262              aa 270
                                                    |===                |===
Gly Ala Pro Arg Cys Gln Cys Pro Ala Gly Ala Ala Leu Gln Ala Asp Gly Arg Ser Cys Thr Ala Ser Ala Thr Gln Ser Cys
GGGGCTCCCCGCTGCCAGTGCCCAGCCGGGGCGCCCTGCAGGCAGACGGCCGCAGCTGCCTCCTGCCACGCATCCGCGACGCAGTCCTGC
CCCGAGGGGCGACGGTCACGGTCGGCCGCGGGACGTCCGTCTGCCGGGAGACGTCCGCGAGGACGGTGCCGTAGGCGCTGCGTCAGGACG
                                                                                        1008

EGF-2
=====
Asn Asp Leu Cys Glu His Arg Glu Asp Asp Val Pro Asn Pro Asp Pro Gly Ser Tyr Ser Cys Met Cys Thr Gly Tyr Arg Leu
AACGACCTCTGCGAGCACTCTGCGTTCCGAACCCGACCAGCCGGCTCCTACTCGTGCATGTGCGAGACCGGCTACCGGCTG
TTGCTGGAGACGCTCGTGAAGACGCAAGGTTGGGGCTGGTCGGCCGAGGATGAGCACGTACACGCTCTGGCCGATGGCCGAC aa 305                    aa 311  EGF-3
                            |===                      |===
Ala Ala Asp Gln His Arg Cys Glu Asp Val Asp Asp Cys Ile Leu Glu Pro Ser Pro Cys Pro Gln Arg Cys Val Asn Thr Gln
GCGGCAGACCAACACGGTGCAGGACGTGATGACTGCATACTGGAGCCCAGTCCTGTCCGCAGGCGTGTCAACACAG
CGCCGTCTGGTTGTGGCCACGCTCCTGCACCTATGACCTCGGGTCAGGACGTCGGCACGTTGTGTC
                            1115                    1131
```

```
                                                                              aa 350  EGF-4
                                              aa 343                          |========
Gly Gly Phe Glu Cys His Cys Tyr Pro Asn Tyr Asp Leu Val Asp Gly Glu Cys Val Glu Pro Val Asp Pro Cys Phe Arg Ala
GGTGGCTTCGAGTGCCACTGCTACCCTAACTACGACCTGGTGGACGGCGAGTGTGTGGAGCCCGTGGACCCGTGCTTCAGAGCC
CCACCGAAGCTCACGTGACGATGGGATTGATGCTGACCACCTGCCGCTCACACACCTGGGCACCTGGGACAAGTCTCGG
                                                                                      1252 aa 390  EGF-5
                                aa 386                                  |========
Asn Cys Glu Tyr Gln Cys Gln Pro Leu Asn Gln Thr Ser Tyr Leu Cys Val Cys Ala Glu Gly Phe Ala Pro Ile Pro His Glu
AACTGCGAGTACCAGTGCCAGCCCCTGAACCAAACTAGCTACCTCTGCGTCTGCGCCGAGGGCTTCGCGCCCATTCCCCACGAG
TTGACGCTCATGGTCACGGTCGGGGACTTGGTTTGATTCGATGGAGACGCAGACGCGGCTCCCGAAGCGCGGGTAAGGGGTGCTC
                                                                                      1358
Pro His Arg Cys Gln Met Phe Cys Asn Gln Thr Ala Cys Pro Ala Asp Cys Asp Pro Asn Thr Gln Ala Ser Cys Glu Cys Pro
CCGCACAGGTGCCAGATGTTTTGCAACCAGACTGCCTGTCCAGCCGACTGCGACCCCAACACCCAGGCTAGCTGTGAGTGCCCT
GGCGTGTCCACGGTCTACAAAACGTTGGTTCTGACGGACAGGTCGGCTGACGCGACAGGTCGGGTTGTGGGTCCGATCGACACTCACGGGA
                                                                  1368
                                      aa 421                                 aa 427  EGF-6
                                      |====                                  |========
Glu Gly Tyr Ile Leu Asp Gly Phe Glu Cys Ile Cys Thr Asp Ile Asp Glu Cys Glu Asn Gly Gly Phe Cys Ser Gly Val Cys His
GAAGGCTACATCCTGGACGGCGTTTCATCTGCACGGACATCGACGAGTGCGAAAACGGCGGCTTCTGCTCCGGGGTGTGCCAC
CTTCCGATGTAGGACCTGCCGCAAAGTAGAGACGCTGCCTGTAGCTGCTCACGCTTTTGCCGCCGAAGACGAGGCCCACAGGTG
                                                        1453                         1469

Asn Leu Pro Gly Thr Phe Glu Cys Ile Cys Gly Pro Asp Ser Ala Leu Ala Arg His Ile Gly Thr Asp Cys Asp Ser Gly Lys
AACCTCCCGGGTACCTTCGAGTGCATCTGCGGGCCCGACTCGGCCCTTGCCCGCCACATTGGCACCGACTGTGACTCCGGCAAG
TTGGAGGGCCATGGAAGCTCACGTAGACGCCCGGGCTGAGCGCCGGGAACGGGCGGTGTAACCGTGGCTGACACTGAGGCCGTTC
                                                                                      1586

O-Linked Glycosylation Domain (starts at aa 463)

Val Asp Gly Gly Asp Ser Gly Ser Gly Glu Pro Pro Pro Ser Pro Thr Pro Gly Ser Thr Leu Thr Pro Pro Ala Val Gly Leu
GTGGACGGTGGCGACAGCGGCTCTGGCGAGCCCCCAGCGCCCGGCTCCACCTTGACTCCTCCCGGCCGTGGGGTC
CACCTGCCACCGCTGTCGCCGAGACCGCTCGGGGCCGAGGTCGGGCTGCCGGGCCGAGGTGAACTGAGGAGGCCGCACCCGAG aa 497    Stop Transfer Sequence                                   aa 520
         |----   --  --  --  --  --  --  --  --  --  --  --  --  --  --  --  --  --  --  --|
         Val His Ser Gly Leu Leu Ile Gly Ile Ser Ile Ala Ser Leu Cys Leu Val Val Ala Leu Leu Ala Leu Leu Cys His Leu Arg
```

```
GTGCATTCGGGCTTGCTCATAGGCATCTCCATCGCGGAGCCTGTGCCTGGTGGCGCTTTTGGGCGCTCTCCTGCCACCTGCGC
CACGTAAGCCCGAACGAGTATCCGTAGAGGTAGCGCTCGGACACGGACCACCACCGCGAAAACCGGAGGAGACGGTGGACGCG
     1690

Cytoplasmic Domain (starts at aa 521)
Lys Lys Gln Gly Ala Ala Arg Ala Lys Met Glu Tyr Lys Cys Ala Ala Pro Ser Lys Glu Val Val Leu Gln His Val Arg Thr
AAGAAGCAGGGCGCGCGCCAGGGCCAAGATGGAGTACAAGTGCGCGGCCCCTTCCAAGGAGGTAGTGCTGCAGCACGTGCGGACC
TTCTTCGTCCCGCGCGCGGTCCCGGTTCTACCTCATGTTCACGCGCCGGGGAAGTTCCTCCATCACGACGTCGTGCACGCCTGG aa 557
Glu Arg Thr Pro Gln Arg Leu OP
GAGCGGACGCCGCAGAGACTCTGAGCGGCCTCCCGTCCAGGAGCCTGGCTCCTGCCTCCTCACCCCCAGCTT
CTCGCCTGCGGGCGTCTCTGAGACT

TGCTACCAAAGCACCTTAGCTGGCATTACAGCTGGAGAAGACCCTCCCCGCACCCCCAAGCTGTTTCTTCTATTC
```

TABLE 2 t-PA Signal Sequence

−32 aa

Met Asp Ala Met Lys Arg Gly Leu Cys Cys Val Leu Leu Leu Cys Gly Ala Val Phe
ATGGATGCAATGAAGAGAGGGCTCTGCTGTGTGCTGCTGCTGTGTGGAGCAGTCTTC
TACCTACGTTACTTCTCTCCCGAGACGACACACGACGACGACACACCTCGTCAGAAG

−13 aa                                                              −1|+1
Val Ser Pro Ser Glu
Glu Ile His Ala Arg Phe Arg Arg Gly Ala Arg
GTTTCGCCCAGCCAG| INTRON
A| GAAATCCATGCCCGATTCAGAAGAGGAGCCAGA
CAAAGCGGGTCGGTC
CTTTAGGTACGGGCTAAGTCTTCTCCTCGGTCT
+4
Ser
TCC
AGG

Hypodermin A Signal Sequence - pHY1

Met Leu Lys Phe Val Ile Leu Leu Cys Ser Ile Ala Tyr Val
COD #1198
<u>GATC</u>ATGCTCAAGTTTGTTATTTTATTGTGCAGTATTGCCTATGTT
　　　BamHI
TACGAGTTCAAACAATAAAATAACACGTCATAACGGATACAA

Phe Gly Ala Val Val Pro Arg Ser Pro Arg
TTCGGTGCCGTCGTACCAAGATCTCCCCGG
AAGCCACGGCAGCATGGTT<u>CTAGA</u>GGGGCC<u>CATGG</u> COD #1199
　　　　　　　　　　　BglII　　　　　KpnI

TABLE 3

| Transfer Vector | TM a.a. Region | Domain |
|---|---|---|
| pTMHY101 | aa 221–462 | EGFs 1–6 |
| pTMHY102 | aa 216–468 | EGFs 1–6 |
| pTMHY103 | aa 216–464 | EGFs 1–6 |
| pTHR10 | aa 227–462 | EGFs 1–6 |
| pTHR11 | aa 227–462:227–462 | EGFs 1–6 + EGFs 1–6 |
| pTHR22 | aa 350–462 | EGFs 4,5&6 |
| pTHR24 | aa 227–462 | EGFs 1–6 + t-PA |

TABLE 3-continued

| Transfer Vector | TM a.a. Region | Domain |
|---|---|---|
| pTHR25 | aa 227–462 | t-PA + EGFs 1–6 |
| pTHR45 | aa 350–421 | EGFs 4&5 |
| pTHR55 | aa 227–421 | EGFs 1–5 |
| pTHR56 | aa 227–386 | EGFs 1–4 |
| pTHR57 | aa 227–343 | EGFs 1–3 |
| pTHR78 | aa 227–497 | EGFs 1–6 + O-linked glycosylation |

TABLE 4

COD #1292
　　　　aa 427
　　　　　Cys Glu Asn Gly Gly Phe
5'ATC<u>GGATCCT</u>GCGAAAACGGCGGCTCC primer/coding sequence
　　　BamHI COD #1293
　　　　aa 350
　　　　　Cys Phe Arg Ala Asn Cys
5'GTG<u>GGATCCT</u>GCTTCAGAGCCAACTGC primer/coding sequence
　　　BamHI COD #1294
　　　　aa 390
　　　　　Cys Asn Gln Thr Ala Cys
5'CAG<u>GGATCCT</u>GCACCCAGACTGCCTGT primer/coding sequence
　　　BamHI COD #1408
aa 339
　Leu Val Asp Gly Glu Cys
5' (CTGGTGGACGGCGAGTGT) coding sequence
　　GACCACCTGCCGCTCACACACCG<u>CCGG</u>CGCCT primer sequence
　　　　　　　　　　　　　　　　　　NotI COD #1490
aa 456
　Arg His Ile Gly Thr Asp Cys
5' (CGCCACATTGGCACCGACTGT) coding sequence
　　GCGGTGTAACCGTGGCTGACATCTCG<u>CCGG</u>CGTAG primer sequence
　　　　　　　　　　　　　　　　　　　NotI TABLE 4-continued COD #1410
aa 381
  His  Glu  Pro  His  Arg  Cys
5' (CACGAGCCGCACGGACGT) coding sequence
    GTGCTCGGCGTGTCCACGGTCTCGCCGGCGTT primer sequence
                                 NotI COD #1411
aa 456
  Arg  His  Ile  Gly  Thr  Asp  Cys  STOP
5' (CGCCACATTGGCACCGACTGTTGA) coding sequence
    GCGGTGTAACCGTGGCTGACAACTCGCCGGCGT primer sequence
                                 NotI COD #1412
aa 416
  Asp  Asp  Gly  Phe  Ile  Cys
5' (GACGACGGTTTCATCTGC) coding sequence
    CTGCTGCCAAAAGGATACGCGCGGCCGGCTG primer sequence
                               NotI COD #1433
aa 339
  Leu  Val  Asp  Gly  Glu  Cys  STOP
5' (CTGGTGGACGGCGAGTGTTGA) coding sequence
    GACCACCTGCCGCTCACAATCCGCCGGCGCCT primer sequence
                               NotI COD #1434
aa 381
  His  Glu  Pro  His  Arg  Cys  STOP
5' (CACGAGCCGCACGGACGTTGA) coding sequence
    GTGCTCGGCGTGTCCACGATCCGCCGGCGTT primer sequence
                               NotI COD #1435
aa 416
  Asp  Asp  Gly  Phe  Ile  Cys  STOP
5' (GACGACGGTTTCATCTGCTGA) coding sequence
    CTGCTGCCAAAAGGATACGATCCGCCGGCGGCTG primer sequence
                               NotI COD #1480
aa 462
  Cys  Asp  Ser  Gly  Cys  Val  Asp  STOP
5' (TGTGACTCCGGCAAGGTGGACTGA) coding sequence
    ACACTGAGGCCGTTCCACCTGACTCTTAAGCT primer sequence
                               EcoRI COD #1479
aa 459
  Gly  Thr  Asp  Cys  Asp  Ser  STOP
5' (GGCACCGACTGTGACTCCTGA) coding sequence
    CCGTGGCTGACACTGAGGACTCTTAAGCAG
                              EcoRI COD #1478
       aa 216
         His  Trp  Ala  Arg  Glu  Ala  Pro
5'CCATGGCCACTGGGCCAGCGAGGCGCCG primer/coding sequence
  BalI COD #1481
aa 490
  Pro  Ala  Val  Gly  Leu  Val  His  Ser  STOP
5' (CCGGCCGTGGGGCTCGTGCATTCGTGA) coding sequence
    GGCCGGCACCCCGAGCACGTAAGCACTCGCCGGCGGTA primer seq.
                                 NotI

TABLE 5

Primers for replacing the Methionine at aa 291
Native Sequence
  Pro  Asp  Gln  Pro  Gly  Ser  Tyr  Ser  Cys  Met  Cys  Glu  Thr  Gly  Tyr  Arg  Leu  Ala  Ala
CCCCGACCAGCCGGGCTCCTACTCGTGCATGTGCGAGACCGGCTACCGGCTGGCGGCC
G
CCCCGACCAGCCGGGCTCCTACAGCTGCCTGTGCGAGACCGGCTACCGGCTGGCGGCC
G

TABLE 5-continued

Mutant Primer 1580     Leu
         PvuII

CAGCCGGGCTCCTACTCGTGC<u>CA</u>GTGCGAGAC<u>T</u>GGCTACCGGCTGGCGGCCG

Mutant Primer 1581     Gln
         XcmI

CCCCGACCAGCCGGGCTCCTACTCGTGCG<u>GC</u>ATGCGAGACCGGCTACCGGCTGGCGGCCG

Mutant Primer 1582     Ala
      FspI    SphI

Primers for replacing the Methionine at aa 388

Native Sequence
Pro His Glu Pro His Arg Cys Gln Met Phe Cys Asn Gln Thr Ala Cys Pro Ala
CCCCACGAGCCGCACAGGTGCCAGATGTTTTGCAACCAGACTGCCTGTCCAGCCG
CCCCACGAGCCGCACAGGTGCCAG<u>C</u>TGTTTTGCAACCAGACTGCCTGTCCAGCCG Mutant Primer 1573     Leu
         PvuII CCCCACGAGCCGCACAGGTG<u>T</u>CA<u>AC</u>AGTTTTGCAACCAGACTGCCTGTCCAGCCG Mutant Primer 1583     Gln
         HincII CCCCACGAGCCGCACAGGTGCCAG<u>GCC</u>TTTTGCAACCAGACTGCCTGTCCAGCCG Mutant Primer 1584     Ala
         StuI

What is claimed is:

1. A thrombomodulin analog peptide that retains biological activity after exposure to oxidants at a concentration and under conditions which eliminate biological activity of native thrombomodulin said peptide having the native methionine at position 388 replaced with a leucine wherein position 388 refers to the amino acids as provided in Table 1.

2. An analog peptide of claim 1 wherein the peptide is soluble in aqueous solutions.

3. A analog peptide of claim 1 wherein the analog peptide is bound to a biocompatible polymer.

* * * * *